United States Patent [19]
Coryn et al.

[11] Patent Number: 5,124,266
[45] Date of Patent: Jun. 23, 1992

[54] METHOD AND DEVICE FOR DETERMINING PROTEIN USING CARRIER MATRIX IMPREGNATED WITH POLYMERIZED URETHANE BASED COMPOUNDS AND METHOD OF MAKING THE DEVICE

[75] Inventors: Timothy M. Coryn, Mishawaka; Arthur L. Y. Lau, Granger; Carrie A. Ritucci; David W. Thompson, both of Elkhart, all of Ind.

[73] Assignee: Miles Inc., Elkhart, Ind.

[21] Appl. No.: 470,230

[22] Filed: Jan. 25, 1990

Related U.S. Application Data

[63] Continuation-in-part of Ser. No. 286,225, Dec. 19, 1988, abandoned.

[51] Int. Cl.$^5$ .................. G01N 21/78; G01N 33/68
[52] U.S. Cl. ........................... 436/86; 422/56; 427/2; 435/805; 436/88; 436/169
[58] Field of Search .................. 422/55–57; 435/805; 436/86–88, 169, 170; 427/2, 408, 411, 407.1; 428/241, 243, 260, 270–275, 290

[56] References Cited

U.S. PATENT DOCUMENTS

| | | | |
|---|---|---|---|
| 3,095,277 | 6/1963 | Free et al. | 436/86 X |
| 3,438,737 | 4/1969 | Atkinson et al. | 436/86 |
| 3,485,587 | 12/1969 | Keston | 436/86 |
| 3,704,781 | 11/1972 | Dahl. | |
| 4,298,644 | 11/1981 | Shimizu et al. | 428/91 |

FOREIGN PATENT DOCUMENTS 0017598 10/1980 European Pat. Off. .
2068034 8/1981 United Kingdom .

*Primary Examiner*—Robert J. Hill, Jr.
*Attorney, Agent, or Firm*—Roger N. Coe

[57] ABSTRACT

A test device and method of determining the presence and concentration of proteins, including albumin and Bence Jones proteins, in a test sample are disclosed. The test device includes a test pad comprising a new and improved carrier matrix incorporating an indicator reagent composition capable of interacting with proteins to produce a visually or instrumentally detectable and/or measurable response. The new and improved carrier matrix of the test pad comprises a fibrous, bibulous substrate, such as filter paper, homogeneously impregnated with a polymerized urethane-based compound dispersed in a liquid vehicle comprising an aprotic solvent and an alcohol. The resulting non-greening carrier matrix provides improved color resolution and increased sensitivity to proteins in dry phase test strip assays, thereby affording a more accurate and trustworthy protein assay of liquid test samples, such as urine. The non-greening carrier matrix also essentially eliminates indicator reagent composition runover onto adjacent test pads, such as a pH test pad, in test strips used to assay for more than one analyte. Also disclosed is a method of making the device.

31 Claims, 5 Drawing Sheets

METHOD AND DEVICE FOR DETERMINING PROTEIN USING CARRIER MATRIX IMPREGNATED WITH POLYMERIZED URETHANE BASED COMPOUNDS AND METHOD OF MAKING THE DEVICE

CROSS REFERENCE TO RELATED APPLICATIONS

This is a continuation-in-part application of applicants' copending application Ser. No. 286,225, filed Dec. 19, 1988 now abandoned.

FIELD OF THE INVENTION

The present invention relates to an improved test device and method of assaying a test sample for the presence and concentration of proteins. More particularly, the present invention relates to a new and improved method and device for assaying a liquid, such as urine, for proteins by utilizing a test device having a test pad comprising an indicator reagent composition incorporated into a new and improved carrier matrix, wherein a detectable or measurable response occurs upon contact of the indicator reagent composition incorporated into the carrier matrix with a protein-containing liquid. The new and improved carrier matrix comprises a fibrous, bibulous substrate, such as filter paper, homogeneously impregnated with a polymerized urethane-based compound by a method that essentially eliminates the development of a green background color in the carrier matrix. The new carrier matrix of the present invention provides improved color resolution and increased protein sensitivity by essentially eliminating the interfering green background color often present in dry phase test strips. Consequently, more accurate detection and measurement, either visually or by instrument, of the total protein content of a liquid test sample are achieved. In addition, the present invention relates to incorporating an indicator reagent composition into a non-greening carrier matrix of the present invention to provide a test pad of a test device in an improved method to determine the presence or concentration of proteins, like albumin and Bence Jones proteins, in a test sample by a dry phase, test strip assay procedure. Furthermore, surprisingly and unexpectedly, the non-greening carrier matrix of the present invention also essentially eliminates the problem of indicator reagent composition runover onto adjacent test pads of multi-determinant test strips.

BACKGROUND OF THE INVENTION AND PRIOR ART

Albumin is the most abundant plasma protein, generally constituting slightly over one-half of the total protein in mammalian plasma. In the human body, albumin has the important role of regulating the water balance between blood and tissues, and of functioning as a transport molecule for various compounds, such as bilirubin, fatty acids, cortisol, thyroxine and drugs such as sulfonamides and barbiturates, that are only slightly soluble in water. An albumin deficiency can restrict the transport of slightly water soluble materials throughout the body and a deficiency is signaled in an individual by an abnormal accumulation of serous fluid, or edema. Therefore, it is clinically important to determine whether an individual has a deficiency of serum albumin.

Likewise, it is clinically important to determine if an individual is excreting an excess amount of protein. A normal functioning kidney forms urine in an essentially two step process. Blood flows through the glomerulus, or glomerular region of the kidney. The capillary walls of the glomerulus are highly permeable to water and low molecular weight components of the blood plasma. Albumin and other high molecular weight proteins cannot pass through these capillary walls and are essentially filtered out of the urine so that the protein is available for use by the body. The liquid containing the low molecular weight components passes into the tubules, or tubular region, of the kidney where reabsorption of some urine components, such as low molecular weight proteins; secretion of other urine components; and concentration of the urine occurs. As a result, through the combined processes of the glomerulus and tubules the concentration of proteins in urine should be minimal to non-existent. Therefore, abnormally high amounts of albumin and/or low-molecular weight proteins in urine must be detected and related to a physiological dysfunction.

The relatively high concentration of albumin in the urine of an individual usually is indicative of a diseased condition. For example, the average normal concentration of protein in urine varies from about 2 mg/dL to about 8 mg/dL, with approximately one-third of the total urinary protein being serum albumin. However, in a majority of diseased states, urinary protein levels increase appreciably, such that albumin accounts for from about 60 percent to about 90 percent of the excreted protein. The presence of an abnormal increased amount of protein in the urine, known as proteinuria, is one of the most significant indicators of renal disease, and may be indicative of various other non-renal related diseases.

Therefore, in order to determine if an individual has an albumin deficiency and/or to determine if an individual excretes an excess amount of protein, and in order to monitor the course of medical treatment to determine the effectiveness of the treatment, simple, accurate and inexpensive protein detection assays have been developed. Furthermore, of the several different assay methods developed for the detection or measurement of protein in urine and serum, the methods based on dye binding techniques have proven especially useful because dye binding methods are readily automated and provide reproducible and accurate results.

In general, dye binding techniques utilize pH indicator dyes that are capable of interacting with a protein, such as albumin, and that are capable of changing color upon interaction with a protein absent any change in pH. When a pH indicator dye interacts with, or binds to, a protein, the apparent $pK_a$ (acid dissociation constant) of the indicator dye is altered and the dye undergoes a color transition, producing the so-called "protein-error" phenomenon. In methods utilizing the dye binding technique, an appropriate buffer maintains the pH indicator dye at a constant pH to prevent a color transition of the pH indicator dye due to a substantial shift in pH. Due to the "protein-error" phenomena, upon interaction with the protein, the pH indicator dye undergoes a color transition that is identical to the color change arising because of a change in the pH. Examples of pH indicator dyes used in the dry phase assay of proteins that are capable of interacting with or binding to proteins and exhibiting "protein-error" color transitions include tetrabromophenol blue and tetrachlorophenol-3,4,5,6-tetrabromosulfophthalein.

Although pH indicator dyes have been used extensively in protein assays, several disadvantages still exist in protein assay methods utilizing indicator dyes. For example, methods based upon pH indicator dyes either cannot detect or cannot quantitatively differentiate between protein concentrations below approximately 15 mg/dL. In addition, although several simple semiquantitative tests and several complex quantitative tests are available for the determination of the total protein content in a test sample, the majority of these assay methods, with the notable exception of the simple colorimetric reagent test strip, require the precipitation of protein to make quantitative protein determinations.

The colorimetric reagent test strip utilizes the previously discussed ability of proteins to interact with certain acid-base indicators and to alter the color of the indicator without any change in the pH. For example, when the indicator tetrabromophenol blue is buffered to maintain a constant pH of approximately 3, the indicator imparts a yellow color to solutions that do not contain protein. However, for solutions containing protein, the presence of protein causes the buffered dye to impart either a green color or a blue color to solution, depending upon the concentration of protein in the solution. Consequently, the development of a green background color in the carrier matrix of a dry phase test strip can interfere in the assay for proteins.

Some colorimetric test strips used in protein assays have a single test area consisting of a small square pad of a carrier matrix impregnated with a buffered pH indicator dye, such as tetrabromophenol blue. Other colorimetric test strips are multideterminant reagent strips that include one test area, or test pad, for protein assay as described above, and further include several additional test pads on the same strip to permit the simultaneous assay of other urinary constituents, like pH. For both types of colorimetric test strips, the assay for protein in urine is performed simply by dipping the colorimetric test strip into a well mixed, uncentrifuged urine sample, then comparing the resulting color of the test pad of the test strip to a standardized color chart provided on the colorimetric test strip bottle.

As will be discussed more fully hereinafter, in a multideterminant reagent strip, the protein test pad often is positioned adjacent to the pH test pad. In addition, the reagents incorporated into the protein test pad, buffered at a pH of about 3 to about 4, often runover from the protein test pad onto the pH test pad when the multideterminant test strip is dipped into the urine sample. Consequently, the pH assay is inaccurate because of contamination by the acidic indicator reagent composition used in the protein assay. Surprisingly and unexpectedly, the test device and method of the present invention also essentially eliminate the problem of indicator reagent composition runover.

For test strips utilizing tetrabromophenol blue, buffered at pH 3, as the indicator dye, semiquantitative assays for protein can be performed and are reported as negative, trace, or one "plus" to four "plus". A negative reading, or yellow color, indicates that the urine contains no protein, as demonstrated by the lack of a color transition of the indicator dye. A trace reading may indicate from about 5 to about 20 mg/dL of protein in the urine. The one "plus" to four "plus" readings, signified by color transitions of green through increasingly dark shades of blue, are approximately equivalent to urine protein concentrations of 30, 100, 300, and over 2000 mg/dL, respectively, and serve as reliable indicators of increasingly severe proteinuria. Therefore, eliminating the development of an interfering green background color in the carrier matrix is important for an accurate protein analysis. The elimination of the green background color is especially important when the test sample includes 30 mg/dL or less of protein, because at such a low protein concentration range, the test pad responds to the protein content by exhibiting a green or yellow color.

In accordance with the above-described method, an individual can readily determine, visually, that the protein content of a urine sample is in the range of 0 mg/dL to about 30 mg/dL. However, the color differentiation afforded by the presently available commercial test strips is insufficient to allow an accurate determination of protein content in urine between 0 mg/dL and about 15 mg/dL. The inability to detect and differentiate between low protein concentrations is important clinically because a healthy person usually has a urine protein level in the range of about 10 mg/dL to about 20 mg/dL. Therefore, it could be clinically important to know more precisely the urine protein content of an individual, rather than merely estimating the protein content at some value less than about 30 mg/dL.

Of course, the protein content of a urine sample can be determined more precisely by semiquantitative protein precipitation techniques or by quantitative 24 hour protein precipitation techniques. However, these tests are time consuming and relatively expensive. Furthermore, the precipitation tests must be run in a laboratory by trained personnel, and therefore are unavailable for the patient to perform at home to quickly determine urine protein content and to monitor the success or failure of a particular medical treatment.

Therefore, it would be extremely advantageous to have a simple, accurate and trustworthy method of assaying urine for protein content that allows visual differentiation of protein levels in the ranges of 0 mg/dL to about 10 mg/dL, about 10 mg/dL to about 20 mg/dL, and about 20 mg/dL to about 30 mg/dL, and upwards to between about 100 mg/dL to about 300 mg/dL. By providing such an accurate method of determining urine protein concentration in an easy to use form, such as a dip-and-read test strip, the urine assay can be performed by laboratory personnel to afford immediate test results, such that a diagnosis can be made without having to wait up to one day for assay results and medical treatment can be commenced immediately. In addition, the test strip method can be performed by the patient at home to more precisely monitor low levels of protein in urine and/or the success of the medical treatment the patient is undergoing. Finally, the method and test device used in a protein assay should not adversely affect or interfere with other test pads that are present on a multideterminant test strip.

As will be described more fully hereinafter, the method of the present invention allows the fast, accurate and trustworthy protein assay of urine by utilizing a test strip that includes a test pad comprising a new and improved carrier matrix incorporating an indicator reagent composition. The carrier matrix comprises a fibrous, bibulous substrate, such as filter paper, homogeneously impregnated with a polymerized urethane-based compound. Surprisingly and unexpectedly, the carrier matrix of the present invention essentially eliminates the interfering green background color that can develop on dry phase test strips. The new and improved carrier matrix of the present invention, by essentially eliminating the development of an interfering green background color, enhances the visual color resolution, and therefore the sensitivity, of the assay, thereby allowing urine protein concentrations to be accurately determined at levels of approximately 30 mg/dL or less. In addition, the carrier matrix also essentially eliminates the runover of the protein indicator reagent composition onto adjacent test pads of a multideterminant test strip, thereby improving the accuracy of assays performed by the adjacent test pad, like a pH assay.

In addition, the test device and method of the present invention can be used to determine the presence or concentration of low molecular weight proteins, such as Bence Jones proteins, in a test sample. All prior art assay techniques for low molecular weight proteins involve either immunoelectrophoresis or heat test methods that are time consuming, relatively expensive and are not amenable for use by an individual at home to detect low molecular weight proteins in urine.

Bence Jones proteins belong to a class of urinary proteins having a low molecular weight of approximately 20,000 and that are small enough to pass through the glomerular filters of the kidney. However, the Bence Jones proteins usually are reabsorbed in the tubular section of the kidney. Therefore, the concentration of Bence Jones proteins is negligible in the urine of a healthy person. As a result, a significant amount of Bence Jones proteins in urine generally is clinically significant. Overall, the detection and measurement of the concentration of low molecular weight proteins in urine is important because certain diseases are characterized by the excretion of specific low molecular weight proteins (globulins) rather than by diffuse proteinuria characterized by elevated albumin levels.

For example, the Bence Jones proteins represent a portion of the high molecular weight plasma myeloma globulin, and therefore are found in increased amounts in the urine of more than one-half of the patients suffering from multiple myeloma or leukemia. Bence Jones proteinuria also is found in the urine of many patients suffering from macroglobulinemia and primary systemic amyloidosis. In addition, an increased excretion of a specific globulin that is similar to Bence Jones proteins occurs in Franklin's disease; and patients with renal tubular disorders, such as the Fanconi syndrome, show a substantial increase in the quantity of globulins excreted in the urine. Accordingly, investigators have searched for a simple assay for low molecular weight proteins because the dye-binding method used in presently available commercial test strips is insensitive to low molecular weight proteins, like Bence Jones proteins. Surprisingly and unexpectedly, the method of the present invention provides an improved technique to detect and measure the concentration of low molecular weight proteins, like Bence Jones proteins, by incorporating an indicator reagent composition into a new and improved carrier matrix comprising a fibrous, bibulous substrate homogeneously impregnated with a polymerized urethane-based compound, that effectively resists the development of an interfering green background color.

The Bence Jones proteins differ from all other urinary proteins in that they coagulate upon heating to temperatures between about 45° C. and about 60° C., and then redissolve on further heating to the boiling point of test sample. This peculiar characteristic of Bence Jones proteins has been the basis of all qualitative and semiquantitative determinations for Bence Jones proteins. The dye binding technique used in commercially available test strips has proved insensitive to Bence Jones proteins because the much greater relative concentration of higher molecular weight proteins, such as albumin, in the urine effectively interferes with and masks the presence of Bence Jones proteins. Furthermore, it is inconvenient and costly to separate the albumin from Bence Jones proteins, thereby negating the utility of separating the albumin from the Bence Jones proteins before using a dry phase test strip.

Presently, dry phase test strips are capable of only marginally detecting the presence of Bence Jones proteins in urine. However, incorporating an indicator reagent composition into the improved carrier matrix of the present invention provides an improved assay test pad for the detection of Bence Jones proteins in liquid test samples, such as urine. Overall, the non-greening carrier matrix of the present invention provides improved color resolution of a color transition resulting upon contact of a protein-containing test sample with the indicator reagent composition, therefore improving assay sensitivity and allowing the detection and measurement of proteins, like albumin, in liquid test samples to levels as low as 10 mg/dL.

Proteinuria resulting either from abnormally high albumin levels or the presence of low molecular weight proteins depends upon the precise nature of the clinical and pathological disorder and upon the severity of the specific disease. Proteinuria can be intermittent or continuous, with transient, intermittent proteinuria usually being caused by physiologic or functional conditions rather than by renal disorders. Therefore, accurate assays of urine and other test samples for protein must be available for both laboratory and home use. The assays must permit the detection or measurement of the proteins of interest, either albumin and/or Bence Jones proteins, such that a correct diagnosis can be made and correct medical treatment implemented, monitored and maintained. In addition, it would be advantageous if the protein assay method, both for high molecular weight proteins, like albumin, and low molecular weight proteins, like Bence Jones proteins, could be utilized in a dip-and-read format for the easy and economical, qualitative or quantitative determination of protein in urine or other test samples.

Furthermore, any method of assaying for protein in urine or other test samples must yield accurate, trustworthy and reproducible results by utilizing a method that provides a detectable or measurable color transition as a result of an interaction between the indicator reagent composition and the protein, and not as a result of a competing chemical or physical interaction, such as a pH change or preferential interaction with a test sample component other than protein. Moreover, it would be advantageous if the protein assay method is suitable for use in dry reagent strips for the rapid, economical and accurate determination of protein in urine and other test samples. Additionally, the method and test pad, comprising the carrier matrix and the indicator reagent composition, utilized in the assay for protein, and the indicator reagent composition, should not adversely affect or interfere with the other test reagent pads that are present on multideterminant test pad strips.

Prior to the present invention, no known method of assaying urine or other test samples for proteins utilized a test device including a test pad comprising a non-greening carrier matrix, comprising a fibrous, bibulous substrate homogeneously impregnated with a polymerized urethane-based compound. The carrier matrix provides improved color resolution and increased assay sensitivity compared to test pads absent the homogeneous impregnation of the polymerized urethane-based compound, such that accurate and trustworthy protein assays can be made for protein concentrations of about 30 mg/dL and below. Furthermore, no other test device includes a test pad that so effectively resists the runover, or bleeding, of the indicator reagent composition onto adjacent test pads that interferes with the assay performed by the adjacent test pad.

In addition, although a dry phase chemistry test strip utilizing a dye, such as tetrabromophenol blue or tetrachlorophenol-3,4,5,6-tetrabromosulfonephthalein, has been used extensively for several years, no dry phase test strip has utilized a test pad comprising a non-greening and non-bleeding carrier matrix comprising a fibrous, bibulous substrate, such as filter paper, homogeneously impregnated with a polymerized urethane-based compound. The non-greening carrier matrix is manufactured by a method that essentially eliminates the development of an interfering green background color of the carrier matrix, therefore improving visual color resolution and increasing assay sensitivity, especially at lower protein concentration levels. Furthermore, until the method of the present invention, dry phase test strip procedures were available principally to test for total protein concentration, i.e., for albumin, only down to levels as low as 30 mg/dL. However, surprisingly and unexpectedly, because of the essential elimination of the interfering green background color, the method of the present invention facilitates the dry phase test strip assay of urine and other test samples for albumin down to levels as low as 10 mg/dL, and for the presence of low molecular weight proteins, such as Bence Jones proteins. Moreover, the carrier matrix of the present invention essentially eliminates the indicator reagent composition from bleeding onto adjacent test pads and interfereing with the adjacent test pad assay.

The prior art contains numerous references on the wet phase and the dry phase chemistry utilized in the pH indicator dye method of assaying urine for proteins. For example, Keston U.S. Pat. No. 3,485,587 discloses the basic dye binding technique used to assay for proteins at a constant pH. Keston teaches utilizing a single indicator dye, maintained at a constant pH slightly below the $pK_a$ (acid dissociation constant) of the dye and impregnated into a dry test paper, like filter paper, to determine the presence or concentration of albumin by monitoring the color transition of the dye. Free, et al., in U.S. Pat. No. 3,095,277, also discloses a method of detecting the albumin content of liquid test samples by incorporating a suitable indicator composition into a bibulous carrier, like untreated filter paper. Similarly, Atkinson et al in U.S. Pat. No. 3,438,737 discloses a test device comprising a test composition impregnated into an untreated bibulous matrix, such as filter paper, wood strips, synthetic plastic fibrous materials, non-woven fabrics and woven fabrics for detecting protein in fluids.

Some investigators have treated a fibrous, bibulous substrate, like paper, with a polyurethane. For example, Isgur et al, in G.B. 2,068,034, disclosed treating paper with a polyurethane polymer amine salt, then curing the polyurethane polymer amine salt at from 104° C. to 150° C. The treatment with the polyurethane polymer amine salt increased the wet strength of paper, cartons, cardboard and related products. Similarly, Daude et al, in EP 17598 disclosed a method of improving the mechanical properties of paper, cardboard and related products, either in the wet stage or the dry stage, by impregnating the paper product with an aqueous emulsion including a blocked polyurethane prepolymer and a deblocking catalyst. The impregnated paper product then is heated at from 150° C. to 350° C. for 0.5 sec. to 6 sec. to deblock the polyurethane prepolymer. In addition, Dahl in U.S. Pat. No. 3,702,781, disclosed a process of impregnating paper with certain polyurethane polymers to strengthen the dry and the wet tensile strength of paper products, and to increase the delamination resistance of paper without a loss of paper flexibility. The polyurethane impregnation was performed by heating a permeable paper product having incorporated therein a composition including a polyisocyanate, a polyol, and a catalyst in an inert solvent.

However, the above-cited references do not teach or suggest, either alone or in combination, that a polyurethane-treated fibrous, bibulous substrate can be used in a diagnostic device to permit a more accurate determination of the amount of an analyte, like protein, and especially low amounts of an analyte, in a test sample. The references also do not teach or suggest, alone or in combination, that a polyurethane-treated fibrous, bibulous substrate effectively eliminates the development of a green background color in the treated substrate or eliminates the bleeding of composition incorporated into the polyurethane-treated fibrous, bibulous substrate from the treated substrate upon contact of the polyurethane-treated substrate with a liquid test sample.

In contrast to the prior art, and in contrast to the presently available commercial test strips, the method of the present invention provides increased sensitivity in the detection and measurement of proteins in a liquid test sample, such as a biological fluid, like urine. Surprisingly and unexpectedly, by utilizing a carrier matrix, comprising a fibrous, bibulous substrate homogeneously impregnated with a polymerized urethane-based compound, that effectively resists the development of a green background color in a dry phase test strip, protein levels of about 30 mg/dL and below can be determined accurately. In addition, the method of the present invention also allows the simple and essentially immediate detection of Bence Jones proteins. Hence, in accordance with the method of the present invention, new and unexpected results are achieved in the dry phase reagent strip assay of urine and other test samples for proteins by utilizing a test pad, comprising an indicator reagent composition incorporated into a non-greening carrier matrix, comprising a fibrous, bibulous substrate homogeneously impregnated with a polymerized urethane-based compound, that effectively resists the development of an interfering green background color. Furthermore, the test device and method of the present invention eliminate assay interferences in multideterminant test strips by eliminating indicator reagent composition runover onto adjacent test pads of the multideterminant test strip.

SUMMARY OF THE INVENTION

In brief, the present invention is directed to a new and improved test device, method of manufacturing the test device, and method of determining the presence or concentration of a component in a test sample. The device includes an improved carrier matrix capable of incorporating an indicator reagent composition that interacts with a test sample component to produce a detectable response. The improved carrier matrix of the test device comprises a fibrous, bibulous substrate homogeneously impregnated with a polymerized urethane-based compound that essentially eliminates the development of an interfering green background color and essentially eliminates the bleeding of the indicator reagent composition from the test pad after contact with the test sample. For home use, the reagent composition produces a visually detectable response. For laboratory use, the reagent composition produces a response that is detectable visually or by instrument.

The new and improved non-greening carrier matrix of the device of the present invention comprises such fibrous, bibulous materials as filter paper that are homogeneously impregnated with a polymerized urethane-based compound. An indicator reagent composition then is homogeneously incorporated into the carrier matrix after homogeneous impregnation of the fibrous, bibulous substrate with a polymerized urethane-based compound. The carrier matrix then holds the indicator reagent composition homogeneously throughout the carrier matrix while maintaining carrier matrix penetrability by the test sample and by the test sample component to be assayed. In accordance with an important feature of the present invention, the indicator reagent composition remains homogeneously dispersed throughout, and does not bleed from, the carrier matrix after contact between the test sample and the test device. Surprisingly and unexpectedly, it has been found that the method used to impregnate the fibrous, bibulous substrate with a polymerized urethane-based compound essentially eliminates the development of an interfering green background color in the carrier matrix, and therefore provides a more accurate and reliable analyte determination.

More particularly, the present invention is directed to a method of assaying urine or other test samples for proteins by utilizing a test device including a test pad comprising an indicator reagent composition and a new and improved carrier matrix that effectively resists the development of an interfering green background color. It has been demonstrated that incorporating an indicator reagent composition into a non-greening carrier matrix, comprising a fibrous, bibulous substrate homogeneously impregnated with a polymerized urethane-based compound according to the method of the present invention, affords improved color resolution and increased sensitivity at low protein concentration ranges by essentially eliminating the development of an interfering green background color. In accordance with an important feature of the present invention, the qualitative or quantitative determination of protein levels between 0 mg/dL and about 2000 mg/dL, and especially between 0 mg/dL and about 30 mg/dL, in urine and other test samples is accomplished. By utilizing the non-greening carrier matrix of the present invention in clinical test methods, the qualitative or quantitative concentration of proteins, such as albumin, in urine or other test samples are more accurately determined because the improved color resolution afforded by the fibrous, bibulous substrate homogeneously impregnated with a polymerized urethane-based compound essentially eliminates the interference resulting from the development of a green background color in the carrier matrix. Consequently, the sensitivity of the dry phase assay method to low concentrations of protein is increased. Furthermore, surprisingly and unexpectedly, the new and improved non-greening carrier matrix of the test device improves the sensitivity of the assay to low molecular weight proteins, such as Bence Jones proteins, in urine and other test samples, thereby providing an improved method to detect low molecular weight proteins.

Therefore, it is an object of the present invention to provide a new and improved test device and method for determining the relative concentration of a chemical compound in a liquid.

Another object of the present invention is to provide a simple, trustworthy, accurate and reproducible method of assaying urine or other liquid test samples for proteins.

Another object of the present invention is to provide a new and improved protein interactive test device for interaction with protein in a test fluid to produce a visible change, such as a change in color, of the test device, indicative of the protein concentration in the test fluid.

Another object of the present invention to provide a method of assaying urine or other liquid test samples for albumin or low molecular weight proteins, such as Bence Jones proteins.

Another object of the present invention is to provide a method of assaying urine or other liquid test samples that provides improved visual color resolution and increased sensitivity to low protein concentrations.

Yet another object of the present invention is to provide a method of assaying urine or liquid test samples that is sensitive to protein concentrations as low as about 10 mg/dL and that quantitatively discriminates between protein levels of from 0 mg/dL to about 2000 mg/dL, and especially from 0 mg/dL to about 30 mg/dL.

Another object of the present invention is to provide a method of assaying urine or other test liquids that utilizes a test device including a test pad comprising a carrier matrix that effectively resists the development of an interfering green background color and comprises a fibrous, bibulous substrate homogeneously impregnated with a polymerized urethane-based compound.

Another object of the present invention is to provide a method of assaying urine or other test liquids by utilizing an indicator reagent composition that, when incorporated into a carrier matrix that effectively resists the development of an interfering green background color and comprises a fibrous, bibulous substrate homogeneously impregnated with a polymerized urethane-based compound, can interact with proteins and undergo a detectable or measurable color transition to establish the presence or to measure the concentration of low levels of protein in the test sample.

Another object of the present invention is to provide a test device including a test pad comprising an indicator reagent composition incorporated into a new and improved, non-greening carrier matrix including a fibrous, bibulous substrate homogeneously impregnated with a polymerized urethane-based compound that can interact with proteins and undergo a visually or instrumentally differentiable color transition to allow the quantitative determination of the concentration of protein in the urine or other liquid samples at levels between 0 mg/dL and about 2000 mg/dL, and especially between 0 mg/dL and about 30 mg/dL.

Another object of the present invention is to provide a test device including a test pad comprising a carrier matrix including a fibrous, bibulous substrate homogeneously impregnated with a polymerized urethane-based compound that essentially eliminates runover of the indicator reagent composition from the test pad onto an adjacent, or nearby, test pad in a multideterminant test strip.

Another object of the present invention is to provide a method of assaying urine or other liquid test samples for the presence or concentration of low molecular weight proteins.

Still another object of the present invention is to provide a method of assaying a liquid sample for low molecular weight proteins, including Bence Jones proteins, by utilizing a test device including a test pad comprising a non-greening carrier matrix, comprising a fibrous, bibulous matrix impregnated with a polymerized urethane-based compound incorporating an indicator reagent composition.

Another object of the present invention is to provide a method of assaying for Bence Jones proteins by incorporating an indicator reagent composition into a dry phase detection device comprising a carrier matrix that effectively resists the development of an interfering green background color and that possesses sufficient sensitivity to allow the detection and measurement of low molecular weight proteins, such as Bence Jones proteins.

Another object of the present invention is to provide a method of manufacturing a detection device for proteins comprising a test pad including a non-greening carrier matrix comprising a fibrous, bibulous substrate homogeneously impregnated with a polymerized urethane-based compound.

Another object of the present invention is to provide a new and improved test device and a method of manufacturing a test device including a test pad comprising a non-greening carrier matrix having incorporated therein, after or during manufacture thereof, an indicator reagent composition capable of interacting with a chemical compound in a test sample, wherein the carrier matrix, comprising a fibrous, bibulous substrate homogeneously impregnated with a polymerized urethane-based compound, effectively resists the development of an interfering green background color and effectively eliminates bleeding of the incorporated indicator reagent composition from the carrier matrix.

Another object of the present invention is to provide a new and improved method of manufacturing a test device used to detect the presence of a chemical compound in a liquid, wherein the chemical compound is capable of permeating a non-greening, non-bleeding carrier matrix comprising a fibrous, bibulous substrate homogeneously impregnated with a polymerized urethane-based compound and is capable of reacting with an indicator reagent composition that is incorporated into the non-greening, non-bleeding carrier matrix.

A still further object of the present invention is to provide a new and improved dry phase test pad that incorporates an indicator reagent composition into a non-greening, non-bleeding carrier matrix comprising a fibrous, bibulous matrix homogeneously impregnated with a polymerized urethane-based compound, that achieves new and unexpected precision in protein response, and that does not interfere with assays performed by adjacent test pads on a multideterminant test strip.

Another object of the present invention is to provide a new and improved test device for the quantitative analysis of proteins in a liquid test sample.

BRIEF DESCRIPTION OF THE DRAWINGS

The above and other objects and advantages and novel features of the present invention will become apparent from the following detailed description of the preferred embodiments of the invention illustrated in the accompanying figures demonstrating the enhanced color resolution of the color transition in the test strips and the increased sensitivity of the test strips to proteins, thereby permitting more accurate quantitative analyte determinations.

DETAILED DESCRIPTION OF THE INVENTION

Figure 1:
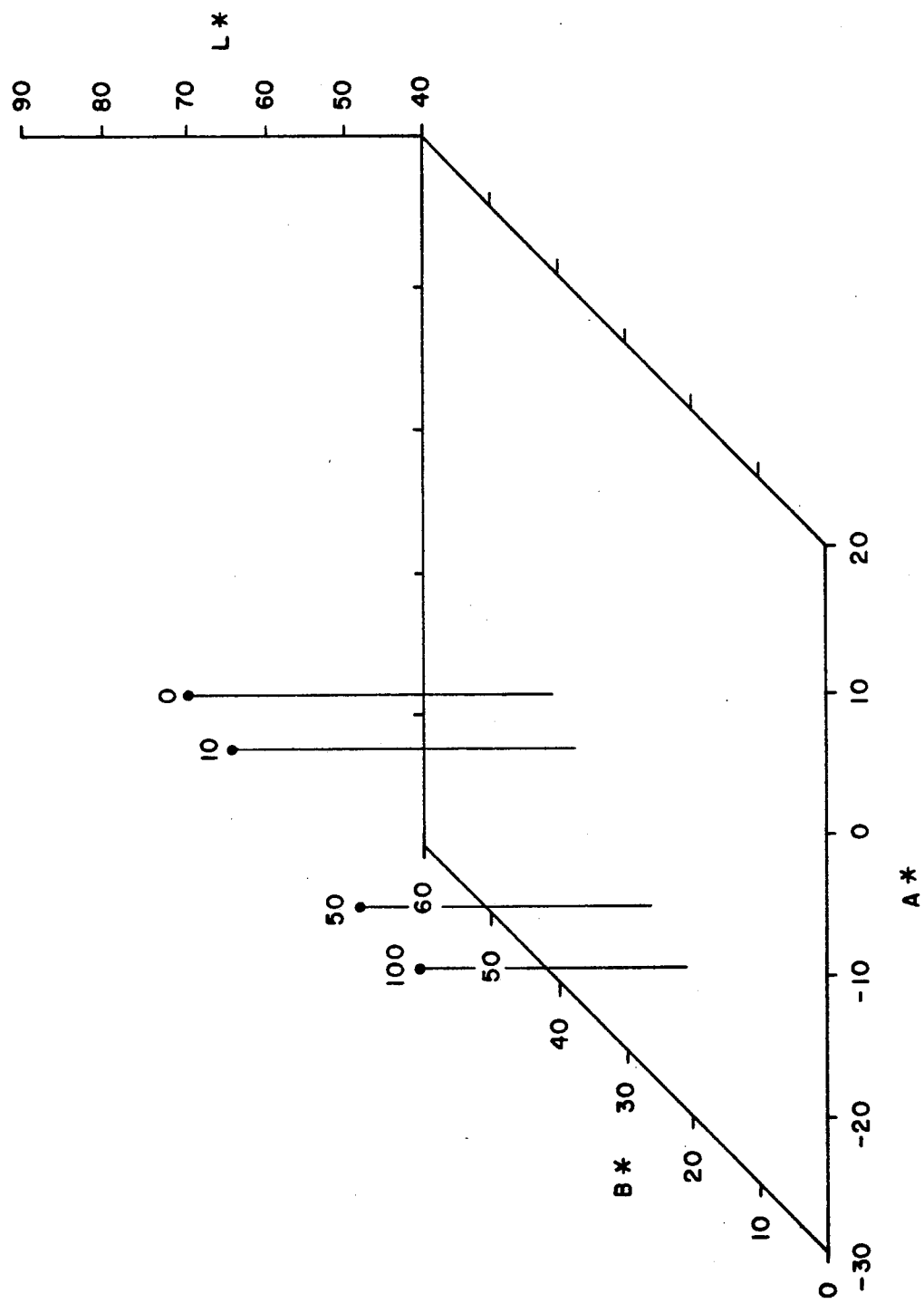
FIG. 1 is a color space plot showing the assay of liquid samples containing 0, 10, 50 and 100 mg/dL of albumin respectively and 100 mg/dL of Bence Jones proteins using a dry phase test strip utilizing a carrier matrix of untreated filter paper incorporating the indicator dye tetrabromophenol blue (TBPB)

In accordance with the method of the present invention, the qualitative or quantitative assay for proteins, including albumin and/or low molecular weight proteins, in urine and other liquid test samples is accomplished by utilizing a test device including a test pad comprising a carrier matrix incorporating an indicator reagent composition. The carrier matrix comprises a fibrous, bibulous substrate homogeneously impregnated with a polymerized urethane-based compound that effectively resists the development of an interfering green background color and that essentially eliminates bleeding of the indicator reagent composition from the test pad.

By using a test device that includes a test pad comprising the new and improved non-greening, non-bleeding carrier matrix, visual color resolution is improved over assays employing a test pad comprising an untreated fibrous, bibulous substrate as the carrier matrix and over assays employing a test pad comprising a treated fibrous, bibulous substrate susceptible to developing an interfering green background color as the carrier matrix. Consequently, the sensitivity of the assay to low protein concentrations is increased when the non-greening carrier matrix is utilized in a test device. The non-bleeding feature of the carrier matrix of the present invention precludes the indicator reagent composition used in the protein assay from interfering with assays performed on adjacent test pads in a multideterminant test strip. The improved color resolution, and the increased sensitivity to low protein levels, afforded by the non-greening carrier matrix of the present invention, and the non-bleeding feature of the carrier matrix, are especially useful in urine assays.

Present-day commercial assays are incapable of differentiating between protein levels ranging from 0 mg/dL to about 30 mg/dL, and especially from 0 mg/dL to about 15 mg/dL. Differentiating between low protein concentration levels is clinically important in the art because a range of from about 10 mg/dL to about 20 mg/dL is used as the normal urine protein level for a healthy individual. Therefore urine protein levels from 0 mg/dL to about 10 mg/dL may indicate a potential protein deficiency that can cause physiological imbalances, and urine protein levels greater than about 20 mg/dL may indicate an excessive excretion of proteins that can signify a diseased state. It should be noted that in regard to urine protein concentrations in the relatively high range, such as from about 100 mg/dL to about 2000 mg/dL, the method of the present invention still affords improved color resolution and increased sensitivity to urine protein concentration, however such clinical benefits are less critical in this concentration range since such high protein levels are definitely indicative of an abnormal physiological state that must be investigated further.

In further regard to urine assays, the presence of low molecular weight proteins, such as Bence Jones proteins, is indicative of specific diseased states, such as leukemia or multiple myeloma. Therefore, in accordance with another important feature of the device and method of the present invention, the improved color resolution afforded by the use of a non-greening carrier matrix comprising a fibrous, bibulous matrix homogeneously impregnated with a polymerized urethane-based compound, and incorporating an indicator reagent composition, increases assay sensitivity to low levels of protein in urine and provides an improved technique to detect low molecular weight proteins in urine. Accordingly, and as will be discussed more fully hereinafter, a method and device is available to test either for total urine protein content in urine, for the albumin content in urine, or for the presence of low molecular weight proteins in urine.

Furthermore, it will become apparent that in addition to assaying urine, the method and device of the present invention also can be used to determine the presence or quantitive concentration of albumin in blood plasma and serums; and more generally, the albumin content of many other albumin-containing fluids as well. In accordance with another important feature of the present invention, the method and device of the present invention are employed in dry phase, test strip assays to determine the presence or concentration of proteins in urine or other liquid test samples. Furthermore, the method and device of the present invention essentially eliminate bleeding of the indicator reagent composition from the carrier matrix, thereby precluding interferences with adjacent test pad assays performed by multideterminant test strips.

Surprisingly and unexpectedly, it has been found that a test pad comprising a suitable indicator reagent composition incorporated into a non-greening carrier matrix of the present invention has demonstrated improved color resolution and increased sensitivity to low protein concentrations when used in a dye-binding technique to determine the presence or concentration of proteins in a test sample. The dye-binding technique using an indicator reagent composition incorporated into the non-greening carrier matrix of the present invention provides a more accurate, trustworthy and clinically significant quantitative assay for protein. Presently, dry phase test strip assays utilize untreated bibulous substrates, such as filter paper, as the carrier matrix, or utilize treated bibulous substrates that are prone to developing an interfering green background color, as the carrier matrix of a test pad used to determine the presence or concentration of protein in a test sample.

The indicator reagent compositions used in present day assay methods for protein interact with proteins and undergo a color transition due to the protein-error phenomena when maintained at the proper, constant pH. The protein-error phenomena is fully described in Free et al U.S. Pat. No. 3,095,277; Atkinson et al U.S. Pat. No. 3,438,737; and Keston U.S. Pat. No. 3,485,587, wherein the various dyes, the correct pH ranges, the buffers and the untreated carrier matrices, such as bibulous substrates, like filter paper, required to observe the protein-error phenomena are disclosed. The three above-identified patents basically describe the present day, dry phase test strips employed to assay for total protein content in urine. These total protein test strips generally include an indicator reagent composition comprising an indicator dye that normally undergoes a color transition at a strongly acidic pH of 5 or below and a buffer to maintain the pH of the indicator dye slightly below the pH of color transition for the dye. A sufficient buffering of the indicator dye essentially assures that the dye changes color due to an interaction with protein rather than due to a pH change occurring upon contact with the test sample. The present day total protein test strips further include a carrier matrix, usually untreated filter paper, for incorporation of the indicator reagent composition.

In accordance with an important feature of the present invention, it has been demonstrated that a new and improved carrier matrix, comprising a fibrous, bibulous substrate, such as filter paper, homogeneously impregnated with a polymerized urethane-based compound, effectively resists the development of an interfering green background color and therefore provides a more accurate and trustworthy assay for total protein content in liquid samples. Furthermore, both suprisingly and unexpectedly, by incorporating an indicator reagent composition in a dry phase test strip comprising a carrier matrix that effectively resists the development of an interfering green color, the detection and measurement of low molecular weight proteins in a test sample is possible. Furthermore, a method of fast, accurate, reproducible and trustworthy assays, performable at home or in the laboratory to yield essentially immediate assay results for albumin or low molecular weight proteins, is achieved. In addition, the method and device of the present invention essentially eliminate interferences with assays performed by adjacent test pads on a multideterminant test strip by essentially eliminating bleeding of the indicator reagent composition from the carrier matrix.

In accordance with an important feature of the present invention, the non-greening carrier matrix of the present invention must incorporate an indicator reagent composition including a suitable indicator dye. A suitable indicator dye is capable of interacting with proteins, and is capable of undergoing a sufficient color transition due to the protein-error phenomena upon interaction with a protein, to give a detectable or measurable response. However, in accordance with the present invention, it has been found that incorporating a suitable indicator reagent composition into a non-greening, non-bleeding carrier matrix, comprising a fibrous, bibulous substrate homogeneously impregnated with a polymerized urethane-based compound, substantially improves the color resolution and differentiation, both visually and instrumentally, of the color transition occurring upon interaction of the indicator dye with proteins. Therefore, the sensitivity of the protein assay, especially at relatively low protein concentrations, is increased because of the homogeneous impregnation of a polymerized urethane-based compound into the carrier matrix and because of the non-greening nature of the carrier matrix of the present invention.

The method of the present invention utilizes the "protein-error" phenomena previously discussed. However, the incorporation of a suitable indicator reagent composition into the non-greening carrier matrix of the present invention improves the color resolution and differentiation of the color transition occurring because of the dye-protein interaction. As previously described, when a pH indicator dye interacts with a protein, the apparent pKa of the dye is altered and a color transition occurs producing the so-called "protein-error" phenomenon. However, by employing the carrier matrix of the present invention, not only is a more spectacular color development achieved because of the impregnation of a polymerized urethane-based compound onto the fibrous, bibulous matrix, but also because the carrier matrix effectively resists the development of an interfering green background color. Consequently, color resolution and color differentiation upon interaction of the indicator dye with proteins is improved, and, accordingly, assay sensitivity is increased.

It has been demonstrated that the non-greening, non-bleeding carrier matrix of the present invention, because of the impregnated urethane-based compound, provides a better blank assay (for a sample containing no protein) by shifting the color transition of a blank, control assay towards the yellow region of the color space. Thus, by further essentially eliminating the development of an interfering green background color, the control assay is maintained at the yellow region of the color space. As a result, by providing a better blank test and by essentially eliminating the development of an interfering green background color, the color resolution and color differentiation of the color transition resulting from an albumin-containing test sample is improved because a more spectacular color development is achieved in comparison to the albumin-free control assay.

In general, any pH indicator dye can be utilized in the method of the present invention, provided that the dye is capable of interacting with proteins and undergoing a detectable and measurable color transition in response to the protein interaction. Such indicator dyes as described above are well-known and are utilized in indicator reagent compositions in methods to determine the presence or the concentration of protein in urine or other liquid test samples. In addition to the indicator dyes, it is known that the indicator reagent composition also may require a sufficient amount of a proper buffer, such that the indicator dye will not change color as a result of a pH shift, but will change color upon contact and interaction with proteins to accurately establish the presence or the concentration of protein in the test sample. Further, it has been demonstrated that any of various known types of buffers can be used in the indicator reagent composition. In addition, it has been found that for optimum results, the pH of the indicator reagent composition generally should be maintained at a pH value only slightly below the pH range wherein the indicator dye of the indicator reagent composition undergoes a color transition. A method of determining a suitable buffered pH value for the particular indicator dye of the indicator reagent composition and of determining the particular buffer that can be used in the indicator reagent composition is found in Keston, U.S. Pat. No. 3,485,587.

Upon contact with the urine or other test sample, a color transition of the indicator reagent composition demonstrates the presence of protein. Furthermore, the intensity and degree of the color transition can be used to determine the concentration of protein in the test sample by comparing or correlating the color produced by the test sample to colors produced by solutions having a known concentration of protein. In accordance with an important feature of the present invention, it has been demonstrated that the intensity and degree of color transition of the indicator reagent composition are surprisingly and unexpectedly increased when the indicator reagent composition is incorporated into a carrier matrix comprising a fibrous, bibulous substrate homogeneously impregnated with a polymerized urethane-based compound. It further has been demonstrated that by impregnating the fibrous, bibulous substrate with a polymerized urethane-based compound according to the method of the present invention, the development of an interfering green background color in the carrier matrix has been essentially eliminated. Consequently, the resulting color transition is sufficiently resolved and differentiated such that the amount of protein in the test sample can be measured and accurately determined without the use of color-measuring instruments, such as spectrophotometers or colorimeters. However, if desired, such color-measuring instruments can be used to measure the difference in color degree and intensity between the test sample and a solution of known albumin concentration.

Accordingly, an assay for protein that utilizes a test pad comprising an indicator reagent composition incorporated into the new and improved non-greening carrier matrix of the present invention improves the accuracy and reliability of the assay and also increases physician confidence in the assay. Additionally, because of the number of urine assays for protein being performed at home by the untrained patient, as opposed to trained physicians or technicians in the laboratory, it is imperative to provide accurate and reliable assay methods for protein content in the urine. Similarly, because many assays are performed on multideterminant test strips, the non-bleeding feature of the carrier matrix of the present invention precludes the protein assay from interfering with assays for other urinary constituents performed by adjacent test pads, thereby further increasing physician or patient confidence in the assays.

The dry phase, test strip assay for protein that utilizes a test pad comprising an indicator reagent composition incorporated into the new and improved non-greening, non-bleeding carrier matrix of the present invention is performed in accordance with methods well known in the art. In general, the assay for protein is performed by contacting the urine or other test sample with an analyte detection device that includes a test pad comprising an indicator reagent composition incorporated into the non-greening, non-bleeding carrier matrix of the present invention. The analyte detection device can be dipped into the test sample, or the test sample can be applied to the analyte detection device dropwise. The resulting change in color of the analyte detection device demonstrates the presence of protein; and, if so designed, the resulting color transition can be compared to a standardized color chart to provide a quantitative measurement of the concentration of protein in the urine or test sample.

Typically, the prior art describes the analyte detection device as a test strip designed either as a single test pad test strip (to assay only for a single analyte) or as a multiple test pad test strip (to assay for several analytes simultaneously). For either type of test strip, the test strip includes a support strip, or handle, normally constructed from a hydrophobic plastic, secured to at least one test pad, comprising a bibulous or nonbibulous substrate, incorporating the indicator reagent composition. In general, the bibulous or nonbibulous substrate is an absorbent material that allows the test sample to move, in response to capillary forces, through the substrate to contact the indicator reagent composition and produce a detectable and measurable color transition.

The test pads of the prior art could be any substance capable of incorporating the chemical reagents required to perform the assay of interest, as long as the substrate, either bibulous or nonbibulous in nature, is substantially inert with respect to the chemical reagents, and is porous and/or absorbent relative to the liquid test sample. However, in accordance with an important feature of the present invention, the test pad comprises a carrier matrix comprising a fibrous, bibulous substrate. The expression "fibrous, bibulous substrate" refers to bibulous materials that are insoluble in water and other physiological fluids and that maintain their structural integrity when exposed to water and other physiological fluids. Suitable fibrous, bibulous substrates include filter paper, cellulose, wood, woven fabrics, nonwoven fabrics and the like. Other suitable fibrous, bibulous substrates include cloth; hydrophilic natural polymeric materials, particularly cellulosic material, and especially fiber-containing papers such as filter paper or chromatographic paper; synthetic or modified naturally-occuring polymers, such as cellulose acetate, polyvinyl chloride, polyacrylamide, polyacrylates, crosslinked dextran, agarose, and other such crosslinked and noncrosslinked water-insoluble fibrous, hydrophilic polymers. Hydrophobic and non-absorptive substances are not suitable for use as the fibrous, bibulous substrate included in the carrier matrix of the present invention. The fibrous, bibulous substrate can be of different chemical compositions or a mixture of chemical compositions. The fibrous, bibulous substrate also can vary in regards to smoothness and roughness combined with hardness and softness. However, in every instance, the carrier matrix comprises a fibrous, bibulous, hydrophilic or absorptive material. The fibrous, bibulous substrate of the carrier matrix is most advantageously constructed from fibrous, bibulous filter paper. In contrast, the handle of the test strip usually is formed from hydrophobic, non-absorptive materials such as polyethylene, terephthalate, polycarbonate or polystyrene.

To achieve the full advantage of the present invention, the indicator reagent composition is incorporated into a carrier matrix comprising filter paper as the fibrous, bibulous substrate. The filter paper substrate is homogeneously impregnated with a polymerized urethane-based compound to form the non-greening, non-bleeding carrier matrix of the present invention before the indicator reagent composition is incorporated into the non-greening, non-bleeding carrier matrix. The test pad, comprising the non-greening carrier matrix of the present invention incorporating the indicator reagent composition, then is utilized in a dry phase test strip for the assay of protein in a test sample. The method of the present invention affords an economical, accurate and reliable assay for the total concentration of protein in test samples that can be performed at home or in the laboratory. In addition, the method of the present invention allows detection, differentiation and measurement of low protein concentrations in the test sample therefore making the assay more useful clinically. Furthermore, a test pad comprising the non-greening and non-bleeding carrier matrix of the present invention prevents interferences attributed to indicator reagent composition runover with assays performed by adjacent test pads on multideterminant test strips.

In accordance with the preferred embodiment of the present invention, to perform a dry phase, test strip assay for protein, the non-greening, non-bleeding carrier matrix first is prepared. A fibrous, bibulous substrate, such as filter paper, first is cut into sheets or strips. The filter paper strips or sheets then are impregnated with a composition containing a urethane compound. As will be described more fully hereinafter, the filter paper can be impregnated with a composition containing a polymerizable urethane compound or with a composition containing a polymerized urethane compound. If a polymerizable urethane compound is impregnated onto the filter paper, it is polymerized by a suitable method after impregnation, then cured, to provide the new and improved carrier matrix of the present invention comprising a fibrous, bibulous substrate homogeneously impregnated with a polymerized urethane-based compound. Alternatively, if the fibrous, bibulous substrate is impregnated with a composition including a polymerized urethane compound, the polymerization step can be omitted, and, after curing, the new and improved carrier matrix of the present invention is provided. The ability of the resulting carrier matrix to effectively resist the development of an interfering green background color, and to resist bleeding of the indicator reagent composition from the carrier matrix, is related to the method of impregnating the polymerized urethane-based compound into the fibrous, bibulous substrate.

A suitable indicator reagent composition then is incorporated into the non-greening, non-bleeding carrier matrix by immersing the non-greening carrier matrix into a solution of the indicator reagent composition, or by spraying or spreading the indicator reagent composition onto the non-greening carrier matrix to form the test pad of the test device. The solvent of the indicator reagent composition is removed by oven drying in an air oven maintained at about 50° C. for about 20 to 30 minutes. Alternatively, the indicator reagent composition can be included in the composition containing a urethane compound, and therefore incorporated into the fibrous, bibulous substrate simultaneously with the urethane compound, such that after curing a test pad of the test device is formed. The test pad, comprising the non-greening, non-bleeding carrier matrix incorporating the indicator reagent composition, then is cut to an appropriate size, such as a test pad having dimensions from about 0.25 cm by about 0.5 cm to about 0.5 cm by about 1.0 cm.

The test pad comprising the non-greening carrier matrix incorporating the indicator reagent composition then is secured to an opaque or transparent hydrophobic plastic handle with double sided adhesive tape. The resulting test device, or dry phase test strip, then is dipped into a fresh, uncentrifuged urine sample for a sufficient time to saturate the test pad with the sample. After waiting a predetermined time, such as from about 15 secs. to about 60 secs., the test strip is examined, either visually or by instrument, for a response. The color transition, if any, of the test pad reveals the presence and/or concentration of protein in the urine sample.

Analogous to the prior art, it is well within the experimental techniques of those skilled in the art of preparing test devices to determine the proper balance between size of carrier matrix, the strength of indicator reagent composition solution, the amount of test sample, and the method of introducing the test sample to the test strip, such as by pipetting rather than dipping, in order to design a quantitative assay for protein utilizing the method and composition the present invention.

In many cases simple visual observation of the test strip provides the desired information. If more accurate information is required, a color chart bearing color spots corresponding to various known protein concentrations can be prepared for the particular indicator reagent composition used in the test strip. The resulting color of the test strip after contact with the urine sample then can be compared with the color spots on the chart to determine the protein concentration of the test sample.

If a still more accurate determination is required, a spectrophotometer or colorimeter can be used to more precisely determine the degree of color transition. In addition, the dry phase, reagent strip assay can be made quantitative by employing spectrophotometric or colorimetric techniques, as opposed to visual techniques, in order to measure the degree of color transition more reliably and more accurately, and therefore more accurately measure the concentration of protein in the test sample, especially at lower protein concentrations, such as below 30 mg/dL.

As will be discussed more fully hereinafter, the ability to detect, differentiate between, and measure low concentrations of proteins in a test sample by employing the non-greening, non-bleeding carrier matrix of the present invention, surprisingly and unexpectedly provides a method of assaying for hard-to-detect low molecular weight proteins that may be present in the test sample. For example, the presence of low molecular weight Bence Jones proteins in urine is a diagnostic indication that the patient suffers from leukemia or multiple myeloma. However, according to present day methods, the detection of Bence Jones proteins in urine usually requires a heat and precipitation technique that is expensive and time consuming. Accordingly, until the method of the present invention, no dry phase, test strip technique was available to reliably detect Bence Jones proteins in urine.

Therefore, in accordance with an important feature of the present invention, it has been demonstrated that the presence or concentration of low levels of albumin, or the presence of Bence Jones proteins, in a urine sample can be determined by utilizing a dry phase test strip comprising a test pad incorporating a suitable indicator reagent composition into a non-greening, non-bleeding carrier matrix of the present invention. Surprisingly and unexpectedly, the non-greening, non-bleeding carrier matrix of the present invention provides improved color resolution and differentiation because it effectively resists the development of an interfering green background color, and hence provides improved assay sensitivity compared to matrices used in the prior art.

As previously discussed, a dry phase test strip used for the assay of proteins in test samples generally includes a test pad having carrier matrix comprising a bibulous or non-bibulous substrate that is amenable to incorporation of a suitable indicator reagent composition; that permits the urine or other test sample to permeate the substrate rapidly enough to obtain protein assays relatively quickly; and that does not contaminate the urine or other test sample either by test sample extraction of components comprising the substrate or by appreciably altering the urine or test sample in a way to make the subsequent assays inconclusive, inaccurate or doubtful.

Such a carrier matrix, upon incorporation of a suitable indicator reagent composition, provides a test pad that allows the detection or accurate measurement of protein in liquid test samples. However, the prior art test pads, comprising an indicator reagent composition incorporated into a carrier matrix comprising either an untreated bibulous substrate or untreated nonbibulous substrate, or a carrier matrix comprising a treated bibulous substrate having the tendency to develop a green background color, did not allow the accurate protein determination of test samples containing from 0 mg/dL to about 30 mg/dL of protein. Surprisingly and unexpectedly, unlike the untreated bibulous and nonbibulous substrates of the prior art and unlike the treated bibulous substrates having a tendency to develop a green background color, the new and improved non-greening carrier matrix used in the method and test device of the present invention allows the measurement and detection of low levels of albumin in a test sample, such as from 0 mg/dL to about 30 mg/dL.

For the test strip of the present invention, designed to assay for the total protein content of a test sample, the carrier matrix can be any fibrous, bibulous substrate homogeneously impregnated with a polymerized urethane-based compound that effectively resists the development of a green background color and that allows permeation by the test sample to saturate the test pad of the test strip and to contact the indicator reagent composition. To achieve the full advantage of the present invention, in the assay for the total protein content of a test sample, the non-greening, non-bleeding carrier matrix comprises a fibrous, bibulous substrate, including cellulosic materials, such as paper, and preferably filter paper. Filter paper possesses all of the qualities required of a bibulous matrix of the present invention, plus the advantages of abundant supply, favorable economics, and a variety of suitable grades for impregnation by the polymerized urethane-based compound.

However, in accordance with an important feature of the present invention, the fibrous, bibulous substrate, such as filter paper or other cellulosic bibulous substrates, is homogeneously impregnated with a polymerized urethane-based compound. The untreated filter paper bibulous substrates and the related untreated bibulous substrates of the prior art possess sufficient porosity to allow proteins, such as albumin, to penetrate the bibulous substrate, and contact and interact with the incorporated indicator reagent composition to produce a color transition. By homogeneously impregnating a polymerized urethane-based compound onto a fibrous, bibulous substrate, a carrier matrix possessing sufficient porosity and unexpectedly improved color resolution and differentiation of the color transition results. Therefore, a protein assay of increased sensitivity is provided. Furthermore, it has been found that homogeneously impregnating a polymerized urethane-based compound onto a fibrous, bibulous substrate by the method of the present invention further improves the color resolution and differentiation of the color transition by essentially eliminating the development of an interfering green background color in the carrier matrix. As an additional and unexpected advantage, the impregnated carrier matrix of the present invention essentially eliminates bleeding of the indicator reagent composition from the test pad.

In accordance with an important feature of the present invention, the non-greening, non-bleeding carrier matrix can be prepared by various methods. For example, the fibrous, bibulous substrate first can be homogeneously impregnated with a composition including a polymerized urethane compound dispersed in a suitable liquid vehicle, followed by a curing step to provide a non-greening, non-bleeding carrier matrix homogeneously impregnated with a polymerized urethane-based compound of the desired configuration, such as pore size distribution. Alternatively, the fibrous, bibulous substrate first can be homogeneously impregnated with a composition including a polymerizable urethane compound dispersed in a suitable liquid vehicle. Then, after polymerization of the polymerizable urethane compound, a fibrous, bibulous substrate that is homogeneously impregnated with a polymerized urethane compound results. Similarly, this carrier matrix then is cured to provide a carrier matrix of the desired configuration, such as pore size distribution and pore shape, and that effectively resists the development of an interfering green background color. Consequently, by then incorporating a suitable indicator reagent composition into a non-greening carrier matrix of the present invention, a test pad for a test device and method of detecting or differentiating between low levels of albumin, such as from 0 mg/dL to about 30 mg/dL, and of detecting low molecular weight proteins, in a test sample are provided.

In accordance with another important feature of the present invention, it has been found that the method of impregnating a polymerized urethane-based compound onto a fibrous, bibulous substrate provides a carrier matrix that effectively resists the development of an interfering green background color and that is non-bleeding. Therefore, a test pad comprising a non-greening carrier matrix demonstrates improved color resolution and improved color differentiation when employed in a dry phase, test strip assay for high molecular weight proteins, such as albumin, and for low molecular weight proteins, such as Bence Jones proteins.

As will be demonstrated in the embodiments of the present invention described hereinafter, if the fibrous, bibulous substrate is impregnated with a composition including a polymerizable urethane compound dispersed in a suitable liquid vehicle, the polymerizable urethane compound first is polymerized to yield a polymerized urethane compound. Then the polymerized urethane compound, dispersed in a suitable liquid vehicle, is cured either by a water bath, by a sonicator bath containing water or by heating the polymerized urethane compound to produce the polymerized urethane-based compound. If a polymerized urethane compound is impregnated onto a fibrous, bibulous substrate, the polymerization step is omitted, but the curing step is included in order to provide a non-greening carrier matrix having a polymerized urethane-based compound of the preferred configuration that effectively resists the development of an interfering green background color and that is non-bleeding. Furthermore, in each case, the non-greening carrier matrix comprising a fibrous, bibulous matrix homogeneously impregnated with a polymerized urethane-based compound is treated with a suitable indicator reagent composition before the non-greening carrier matrix is used in a test device to detect proteins.

It has been found that in order to provide the new and improved carrier matrix of the present invention, a polymerizable urethane compound or a polymerized urethane compound, such as a urethane prepolymer, first is dispersed or dissolved in a suitable liquid vehicle. Then the resulting dispersion or solution is impregnated onto the fibrous, bibulous substrate. Similarly, a mixture of a polymerizable urethane compound and a polymerized urethane compound, dispersed or dissolved in a suitable liquid vehicle, can be impregnated onto the fibrous, bibulous substrate. The liquid vehicle is removed from the dispersion or solution during curing of the urethane-containing composition. Removing the liquid vehicle during curing allows the urethane compound to dry and coagulate into the preferred pore size and pore shape on the fibrous, bibulous substrate.

It should be noted that the polymerized urethane-based compound impregnated onto the bibulous substrate shifts a blank test for albumin to the yellow region of the color space, thereby providing a carrier matrix that gives a more spectacular color transition compared to a carrier matrix that is not impregnated with a polymerized urethane-based compound. Furthermore, in accordance with an important feature of the present invention, it was demonstrated that the components comprising the liquid vehicle act to provide a carrier matrix impregnated with a polymerized urethane-based compound that effectively resists the development of an interfering green background color. Overall, the resulting non-greening carrier matrix comprising a polymerized urethane-based compound homogeneously impregnated onto a fibrous, bibulous substrate provides an improved test pad for use in a dry phase test strip designed for the assay of proteins.

The urethane compound dispersed or dissolved in a suitable liquid vehicle can be polymerizable or polymerized, and includes oligomers, prepolymers, incompletely cured polymers and mixtures thereof. In addition, depending upon the solubility and chemical properties of the indicator reagent composition, the urethane-containing composition can be mixed with the indicator reagent composition prior to curing, and the test pad then is formed by curing the urethane-containing composition onto the fibrous, bibulous substrate. The test pad comprising the non-greening, non-bleeding carrier matrix incorporating the indicator reagent composition is cut into strips, then into pads, and secured to a plastic handle.

It has been found that the urethane-containing composition, including a polymerizable or polymerized urethane compound like an oligomer, prepolymer, incompletely cured polymer or mixtures thereof, dispersed in a continuous liquid vehicle forms a cured film on the fibrous, bibulous substrate upon removal of the continuous liquid vehicle phase during the curing process. The urethane compound, after dissolving or dispersing in a continuous liquid vehicle phase, such as by including an emulsifier, can be cured in any known manner. Further, the solution or dispersion of the urethane compound can include a suitable curing catalyst or can be heat cured provided that the solution or dispersion of the urethane compound is homogeneously impregnated onto the fibrous, bibulous substrate in the form of an incompletely-cured solution or dispersion. Generally, urethane compounds useful in accordance with the present invention are those that can be dissolved or dispersed in a liquid vehicle, such as an organic solvent blend, like a blend comprising an aprotic solvent and an alcohol, and that can be cured to yield an essentially colorless film that effectively resists the development of an interfering green background color.

In accordance with one embodiment of the present invention, the urethane compound is a polymerizable urethane prepolymer, and particularly a urethane prepolymer comprising essentially repeating urethane units wherein the prepolymer chain is terminated at each end with isocyanate functionalities. To achieve the full advantage of the present invention, it has been found that the polymerizable urethane compound, or a polymerized urethane compound, is preferentially neutral in electronic character. An example of a suitable commercial urethane prepolymer is DESMODERM KBH GRANULATE, available commercially from BAYER AG.

The expression "urethane prepolymer" is understood to describe an essentially linear polymer of repeating urethane units. The urethane prepolymer has at least two isocyanate functionalities per molecule, and the polyurethane prepolymer should have a weight average molecular weight ($M_w$) of at least about 50,000. Urethane prepolymers with weight average molecular weights below about 50,000, for example down to about 30,000, also are useful as long as the prepolymers are soluble or dispersible in a liquid vehicle and can be cured on the fibrous bibulous substrate. The maximum $M_w$ is one wherein the urethane prepolymer can be solubilized or otherwise dispersed in a continuous liquid vehicle phase, such as a suitable organic solvent blend, like a dimethylformamide and alcohol blend. For the incompletely-cured dispersed urethane prepolymer, weight average molecular weights of up to about 500,000 are expected to be practical for upper limit to the molecular weight of formed polymerized urethane-based compound on the fibrous, bibulous substrate. It has been found that, to achieve the full advantage of the present invention, the $M_w$ for the polymerizable urethane prepolymer is within the $M_w$ range of about 70,000 to about 80,000.

The polymerizable or polymerized urethane compound, such as a urethane prepolymer, useful in the method of the present invention can include other monomeric units that are incorporated into the polymerizable urethane compound by copolymerizing an isocyanate containing monomer, hydroxyl containing monomer and a suitable third monomeric unit into the urethane prepolymer. In addition, although the polymerizable or polymerized urethane compound useful in the method of the present invention is preferentially neutral in nature, anionic or cationic polymerizable urethane compounds also are envisioned as being useful. More particularly, a prepolymer found useful in the method of the present invention, DESMODERM KBH, is a neutral thermoplastic granular polymerized urethane material, obtained by reacting 75 parts of a polyester of adipic acid, including 70 mol % ethylene glycol and 30 mol % 1,4-butanediol ($M_w=2,000$); 25 parts of a polyester of adipic acid and 1,4-butanediol ($M_w=2,250$); 25 parts 1,4-butanediol; and 85 parts diphenylmethanediisocyanate.

In accordance with the present invention, the particular urethane compound utilized in the present invention, after mixing with the components of the urethane-containing composition, such as the continuous liquid vehicle, is cured after impregnation onto the fibrous, bibulous substrate to produce a polymeric film that has a physical structure permeable both to high molecular weight and to low molecular weight proteins, that effectively resists the development of an interfering green background color, and that essentially eliminates bleeding of the indicator reagent composition from the carrier matrix. Generally, the urethane compound is present in the urethane-containing composition in a range of from about 0.1% by weight to about 10% by weight, and preferably from about 1% by weight to about 5% by weight, based upon the total weight of the urethane-containing composition.

As will be discussed more fully hereinafter, the non-greening, non-bleeding carrier matrix of the present invention, comprising a fibrous, bibulous substrate homogeneously impregnated with a polymerized urethane-based compound, affects the degree of color resolution and the sensitivity of the protein assay. Therefore, in accordance with the method of the present invention, analyte test devices including a non-greening carrier matrix of the present invention can be designed for improved color resolution and increased assay sensitivity.

In addition to the urethane compound, the urethane-containing composition used to impregnate the fibrous, bibulous substrate to form the carrier matrix of the present invention may include surfactants to help solubilize or emulsify the urethane compound in the liquid vehicle or to improve the ability of the urethane-containing composition to impregnate the fibrous, bibulous substrate. The surfactants can be present from 0% by weight up to approximately 5% by weight, based on the total weight of the urethane-containing composition. Anionic surfactants found useful in the urethane-containing composition are not necessarily limited to a particular type, and include ammonium, alkylammonium, potassium and/or sodium dodecylbenzene sulfonate, alkyl sulfonates, silylalkyl sulfonates, alkyl sulfates, alkyl ether sulfates, dioctyl sulfosuccinate, alpha olefin sulfonates, and alkyl sarcosinates; or mixtures thereof. Similarly, nonionic surfactants, such as the nonoxynols or octoxynols, as are well known in the art, can be used in the urethane-containing composition.

In addition, other surface active agents, such as silicon-containing materials, like a polydimethylsiloxane fluid, can be incorporated into the urethane-containing composition in weight percentages of up to 2% based upon the total weight of the urethane-containing composition. These silicon-containing materials possess a low surface tension, and therefore further assist in impregnating the fibrous, bibulous substrate and also act to alter the surface tension of the urethane-containing composition to provide a leveling effect to produce a smooth polymerized urethane-based film on the fibrous, bibulous substrate.

As discussed previously, the urethane-containing composition includes a liquid vehicle, such as an organic solvent blend, capable of solubilizing or dispersing the urethane compound and any surfactants or silicon-containing materials that may be present. The liquid vehicle should be relatively inert such that it will not react with the urethane compound, and the liquid vehicle should evaporate at relatively low temperatures to provide a dry carrier matrix after curing of the urethane-containing composition. It has been demonstrated that organic aprotic solvents, such as dimethylformamide, N-methyl pyrrolidone, and dimethyl sulfoxide, or mixtures thereof, provide the required solvency to dissolve and disperse the components of the urethane-containing composition; provide the required inertness to preclude reaction of the liquid vehicle with the urethane compound; and possess the required vapor pressure to yield a solvent-free polymerized urethane-based film impregnated onto the fibrous, bibulous substrate.

In addition, the lower alcohols, such as methyl alcohol, ethyl alcohol and isopropyl alcohol, have been found to possess the necessary inertness and vapor pressure to yield a solvent-free polymerized urethane-based film. The lower alcohols are included in the urethane-containing composition to replace a portion of the organic aprotic solvent. The lower alcohol does not necessarily act as a solvent, but acts as a replacement for the organic aprotic solvent such that less of the organic aprotic solvent can be included in the urethane-containing composition. Accordingly, the impregnated carrier matrix requires less water-curing time to remove the organic aprotic solvent from the carrier matrix. Such lower alcohols therefore are used in combination with the aprotic solvents described above. The liquid vehicle, removed during curing, is included in the urethane-containing composition in an amount of at least about 85%, and preferably is present in an amount of at least about 90%, and up to about 99.9% by weight, based on the total weight of the urethane-containing composition.

In accordance with an important feature of the present invention, it has been found that solubilizing or dispersing the components of the urethane-containing composition exclusively in an organic aprotic solvent, such as dimethylformamide, often causes the carrier matrix to develop an interfering green background color. Surprisingly and unexpectedly, it also has been found that utilizing a liquid vehicle comprising from about 30% to about 70%, and preferably from about 40% to about 50%, by weight of an alcohol, such as methanol, and from about 30% to about 70% by weight of an organic aprotic solvent, like dimethylformamide, effectively eliminates the development of an interfering green background color in the carrier matrix.

In addition to essentially eliminating the "greening" interference, it also has been found that utilizing a liquid vehicle comprising an aprotic solvent and an alcohol reduces the curing time needed to remove the liquid vehicle from the urethane-containing composition. For example, a 10 minute curing time is needed to sufficiently remove a liquid vehicle consisting exclusively of N-methyl pyrrolidone; a 2 minute curing time is needed to sufficiently remove a liquid vehicle consisting exclusively of dimethylformamide; whereas only about 30 seconds is needed to sufficiently remove a liquid vehicle comprising a 60:38 ratio of dimethylformamide to methyl alcohol by weight. Therefore, a suitable choice of liquid vehicle significantly reduces the time needed to complete the curing step and simultaneously essentially eliminates the "greening" interference.

In accordance with an important feature of the present invention, urethane-containing compositions were mixed according to the formulations presented in Examples 1 through 4. As will be discussed more fully hereinafter, the urethane-containing compositions of Examples 1 through 4, then were used to impregnate a fibrous, bibulous substrate of filter paper. After curing, a suitable indicator reagent composition was incorporated into the resulting carrier matrix to form a test pad used to test standard solutions for albumin or Bence Jones proteins by the normal dip-and-read test strip procedure.

| EXAMPLE 1 | | |
|---|---|---|
| DESMODERM KBH (Neutral Urethane) | 2.0% | (by weight) |
| Dimethylformamide | 98.0% | |
| Total | 100.0% | |
| EXAMPLE 2 | | |
| DESMODERM KBH | 2.0% | (by weight) |
| Dimethylformamide | 60.0% | |
| Methyl Alcohol | 38.0% | |
| TOTAL | 100.0% | |
| EXAMPLE 3 | | |
| DESMODERM KBH | 2.0% | (by weight) |
| Dimethylformamide | 50.3% | |
| Ethyl Alcohol | 47.7% | |
| TOTAL | 100.0% | |
| EXAMPLE 4 | | |
| DESMODERM KBH | 2.0% | (by weight) |
| Dimethylformamide | 53.0% | |
| Isopropyl Alcohol | 45.0% | |
| TOTAL | 100.0% | |

In the manufacture of each of the urethane-containing compositions of Examples 1 through 4, the urethane compound was mixed thoroughly into the dimethylformamide until the mixture was homogeneous. Then, the alcohol, such as methyl alcohol, ethyl alcohol or isopropyl alcohol, was added slowly to the homogeneous mixture to provide a urethane-containing composition including 2% by weight of a urethane compound dispersed in a liquid vehicle. Then a fibrous, bibulous substrate, such as WHATMAN CCP500 filter paper, available from Whatman Ltd., Maidstone, Kent, U.K., was impregnated with a urethane-containing composition of Examples 1 through 4 by dipping the filter paper into the urethane-containing composition for approximately 30 seconds. After impregnating the filter paper with a urethane-containing composition of Examples 1 through 4, the urethane-containing composition was cured onto the fibrous, bibulous filter paper by placing the impregnated filter paper into a 24° C. water bath either for 30 seconds, for 1 minute or for 2 minutes. After removing the impregnated filter paper from the water bath, the impregnated filter paper was dried in an 80° C. oven for about 20 min. to complete the curing process. The resulting carrier matrix comprising a fibrous, bibulous substrate homogeneously impregnated with a polymerized urethane-based compound from a urethane-containing composition of Examples 1 through 4, then has incorporated therein an indicator reagent composition, such as tetrabromophenol blue in citrate buffer. After drying in an oven at 50° C. for 15 minutes, the carrier matrix incorporating the indicator reagent composition is cut into test pads.

Although the above-described process is the preferred curing process, alternatively, a urethane-containing composition impregnated onto a fibrous, bibulous substrate can be cured either by placing the impregnated bibulous substrate into a sonicator bath containing water, then sonicating for 30 seconds, 1 minute or 2 minutes, followed by oven drying at 80° C. for about 20 minutes; or by eliminating the water curing step and curing the urethane-containing composition onto the fibrous, bibulous substrate by oven drying at 80° C. for about 20 minutes. It should be noted that the water curing step can be eliminated entirely. However, the performance of a test pad comprising a carrier matrix of the present invention that has been cured in water is superior to a test pad comprising a carrier matrix of the present invention that has not been cured in water. The superior results demonstrated by the water-cured carrier matrix may be attributed to more complete liquid vehicle removal during water curing and to a more preferred polyurethane pore shape and pore size distribution that results from the water curing.

Normally, after curing the urethane-containing composition onto the fibrous, bibulous substrate to form a polymerized urethane-based compound, the resulting carrier matrix of the present invention has an indicator reagent composition incorporated therein to form a test pad. However, if the reagents comprising the indicator reagent composition are soluble in the liquid vehicle used in the manufacture of the urethane-containing composition, like a dimethylformamide and alcohol blend, and if the reagents comprising the indicator reagent composition are insoluble in water, then the indicator reagent composition can be incorporated into the urethane-containing composition and impregnated onto the fibrous, bibulous substrate with the urethane-containing composition prior to curing.

To show the new and unexpected results arising from using a test pad, comprising the non-greening, non-bleeding carrier matrix of the present invention incorporating a suitable indicate reagent composition, in a test device to detect and measure the amount of protein in a test sample, color space plots were made for total protein assays and for Bence Jones protein assays. The assays utilized dry phase test strips including a test pad comprising an indicator reagent composition incorporated into an untreated filter paper bibulous matrix; or utilized dry phase test strips including a test pad comprising an indicator reagent composition incorporated into a carrier matrix comprising a fibrous, bibulous substrate homogeneously impregnated with a polymerized urethane-based compound.

Figure 2:
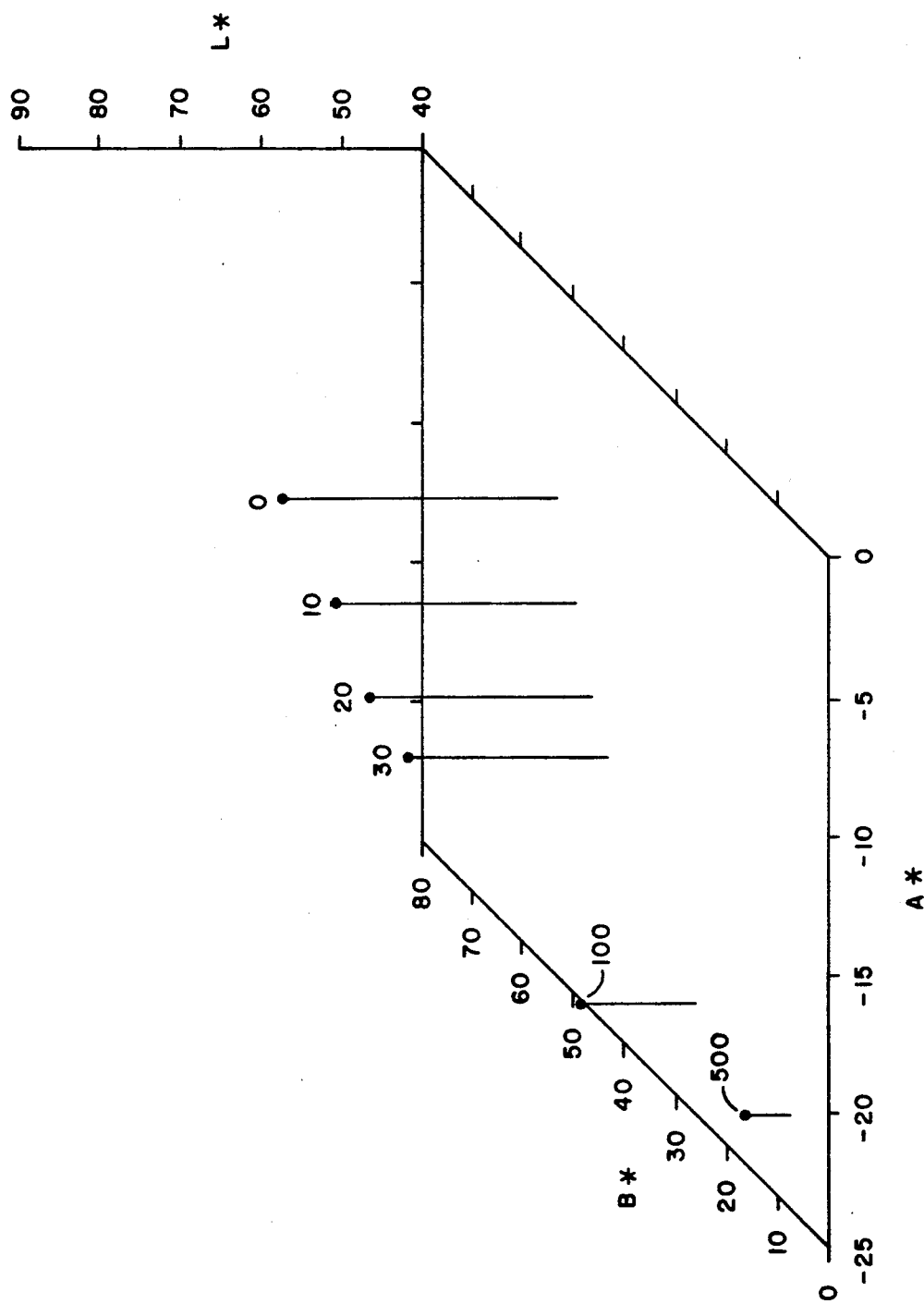
FIG. 2 is a color space plot showing the assay of liquid samples containing 0, 10, 20, 30, 100 and 500 mg/dL of albumin respectively and 100 mg/dL of Bence Jones proteins using a dry phase test strip utilizing a carrier matrix comprising a filter paper substrate homogeneously impregnated with a polymerized urethane-based compound, and incorporating the indicator dye tetrabromophenol blue (TBPB)

FIGS. 1 and 2 are color space plots obtained from contacting four (FIG. 1) or five (FIG. 2) standardized albumin solutions and from contacting a standardized solution of Bence Jones proteins with various dry phase test strips including a test pad comprising an indicator reagent composition impregnated into either a carrier matrix comprising untreated filter paper (FIG. 1) or a carrier matrix comprising a fibrous, bibulous substrate homogeneously impregnated with a polymerized urethane-based compound from the urethane-containing composition of Example 1 (FIG. 2).

For example, FIG. 1 is the color space plot resulting from contacting a dry phase test strip including a test pad comprising tetrabromophenol phenol blue (TBPB) buffered with a citrate buffer as the indicator dye incorporated into an untreated filter paper carrier matrix with standardized solutions containing no albumin (0), 10 mg/dL albumin (10), 50 mg/dL albumin (50), 100 mg/dL albumin (100) and 100 mg/dL Bence Jones proteins (BJ). FIG. 2 is a color space plot for a dry phase test strip including a test pad comprising the identical indicator reagent composition incorporated into a carrier matrix including WHATMAN CCP500 filter paper homogeneously impregnated with a polymerized urethane-based compound from the urethane-containing composition of Example 1. The impregnated filter paper was subjected to a water curing process before incorporation of the indicator reagent composition. The dry phase test strips, including a test pad comprising an indicator reagent composition incorporated into an impregnated carrier matrix, contacted standardized albumin-containing solutions including no albumin (0), 10 mg/dL albumin (10), 20 mg/dL albumin (20), 30 mg/dL albumin (30), 100 mg/dL albumin (100), 500 mg/dL albumin (500) and 100 mg/dL Bence Jones proteins (BJ).

As illustrated in FIGS. 1 through 5, a color space plot includes three axes, the $L^*$, $A^*$ and $B^*$ axes. The values of $L^*$ plotted on the vertical axis are a measure of the intensity of color, whereby a large $L^*$ value denotes a light color and $L^*=0$ denotes a completely black color. The horizontal $A^*$ axis is a measure of the color transition from green to red, whereby the more positive the $A^*$ value, the more red the color, and analogously, the more negative the $A^*$ value, the more green the color. Similarly, the third axis, $B^*$, is a measure of the color transition from blue to yellow, whereby the greater the value of $B^*$, the more yellow the color, and analogously the smaller the value of $B^*$, the more blue the color.

The color space difference ($\Delta E$) is calculated from the following equation:

$$\Delta E = (L_1^* - L_2^*)^2 + (A_1^* - A_2^*)^2 + (B_1^* - B_2^*)^2 \tag{1}$$

wherein:
  $L_1^*$, $A_1^*$, and $B_1^*$ are the color space values determined for a first standardized protein solution;
  $L_2^*$, $A_2^*$ and $B_2^*$ are the color space values determined for a second standardized protein solution having a different protein concentration from the first standardized protein solution; and
  $\Delta E$ is the color space difference between the color space plots of the first and second standardized protein solutions.

The color space difference ($\Delta E$) is the straight line distance between two points in a three-dimensional color space plot. Theoretically, a color space difference of 1 is the smallest color difference the human eye can distinguish. However, because of the inherent differences between the visual capabilities of individuals, a color space difference ($\Delta E$) of about 5 is required in order to practically and confidently distinguish between colors.

The $L^*$, $A^*$ and $B^*$ values plotted on the color space plots of FIGS. 1 and 2 are calculated from the percent reflectance measurements taken at sixteen different wavelengths evenly spaced between 400 nm (nanometers) and 700 nm using standard equations well-known in the art. In general, the percent reflectance at each of the sixteen different wavelengths is multiplied by the intensity of the light at that wavelength. These values then are multiplied by standard weighing functions for the colors red, green and blue, and finally added together These calculations yield three tristimulus values X, Y and Z, and L*, A* and B* are calculated from the X, Y and Z tristimulus values using the following equations:

$$L^* = 116 \times [(Y/Y_o)^{\frac{1}{3}} - 16)] \quad (2)$$

$$A^* = 500 \times [(X/X_o)^{\frac{1}{3}} - (Y/Y_o)^{\frac{1}{3}}] \quad (3)$$

$$B^* = 200 \times [(Y/Y_o)^{\frac{1}{3}} - (Z/Z_o)^{\frac{1}{3}}] \quad (4)$$

wherein:

Xo, Yo and Zo are the tristimulus values for perfect white (i.e. reflectance = 100% at all wavelengths), and X, Y and Z are the tristimulus values calculated as described above from the sixteen wavelengths between 400 nm and 700 nm.

From the color space plots of FIGS. 1 and 2, the color space differences ($\Delta E$) were calculated, and summarized in TABLE I. In interpreting TABLE I, the term, $\Delta E$(Alb 10-0) is the color space difference between protein assays for protein solutions containing 10 mg/dL of albumin and 0 mg/dL of albumin. Similarly, the term $\Delta E$(Alb50-0) is the color space difference between protein assays for protein solutions containing 50 mg/dL of protein and 0 mg/dL of protein. The terms $\Delta E$ (Alb100-0), $\Delta E$ (Alb 500-0) and $\Delta E$ (BJ100-0) are analogously defined.

At best, the assayer could estimate that the sample contained from 0 mg/dL albumin to about 10 mg/dL albumin.

Similarly, FIG. 1 and TABLE I demonstrate that an assayer could not determine the concentration of Bence Jones proteins in a test sample containing from 0 mg/dL of Bence Jones proteins to about 100 mg/dL of Bence Jones proteins because the color space difference between a sample containing 0 mg/dL of Bence Jones proteins and a sample containing 100 mg/dL of Bence Jones protein provided by an analyte detection device having an indicator reagent composition impregnated into an untreated filter paper matrix is only 4.4, or a color space difference that is barely detectable by a normal human eye. TABLE I and FIG. 1 further show that the human eye can detect color differences resulting from the presence of 20 mg/dL, 30 mg/dL, 50 mg/dL and 100 mg/dL of albumin because the color space differences are 9.9, 12.1, 19.2 and 25.5, respectively.

However, surprisingly and unexpectedly, by homogeneously impregnating a fibrous, bibulous filter paper substrate with a polymerized urethane-based compound, the carrier matrix improves the color resolution and differentiation of the color transition to permit an assayer to visually differentiate between samples containing 0 mg/dL of albumin and 10 mg/dL albumin. From FIG. 2 and TABLE I, a color space difference ($\Delta E$) between a solution containing 10 mg/dL of albumin and a solution containing no albumin is 6.6 when

TABLE I

COLOR SPACE DIFFERENCES ($\Delta E$) FOR PROTEIN ASSAYS USING AN INDICATOR REAGENT COMPOSITION INCORPORATED INTO UNTREATED FILTER PAPER AND INTO FILTER PAPER IMPREGNATED WITH A POLYMERIZED URETHANE-BASED COMPOUND

| FIG. NO. | CARRIER MATRIX | $\Delta E$ (Alb10-0) | $\Delta E$ (Alb20-0) | $\Delta E$ (Alb30-0) | $\Delta E$ (Alb50-0) | $\Delta E$ (Alb100-0) | $\Delta E$ (Alb500-0) | $\Delta E$ (BJ100-0) |
|---|---|---|---|---|---|---|---|---|
| 1 | Untreated Filter Paper | 4.8 | 9.9 | 12.1 | 19.2 | 25.5 | 36.1 | 4.4 |
| 2 | Filter Paper Impregnated With Polymerized Urethane-Based Compound of Example 1 | 6.6 | 12.3 | 16.8 | — | 37.2 | 55.6 | 13.0 |

0 = Albumin 0 mg/dL and Bence Jones protein 0 mg/dL
Alb10 = Albumin 10 mg/dL
Alb20 = Albumin 20 mg/dL
Alb30 = Albumin 30 mg/dL
Alb50 = Albumin 50 mg/dL
Alb100 = Albumin 100 mg/dL
Alb500 = Albumin 500 mg/dL
BJ100 = Bence Jones proteins 100 mg/dL As illustrated in the color space plot of FIG. 1 and in TABLE I, protein assays were conducted on standardized solutions including albumin and Bence Jones proteins using a dry phase test strip including a test pad having the indicator, tetrabromophenol blue, incorporated into an untreated filter paper matrix. From FIG. 1 and TABLE I, it was found that the color space difference between a solution containing 10 mg/dL of albumin and a solution containing no albumin is 4.8. Because the human eye normally can differentiate only between colors having a color space difference of approximately 5, this assay would be inconclusive as to whether the sample contained any albumin because the color differentiation between the test strip contacting the 0 mg/dL albumin solution and the test strip contacting the 10 mg/dL test strip could not be accurately determined.

using a test device including a test pad incorporating an indicator reagent composition into a carrier matrix impregnated with a polymerized urethane-based compound. Such a color space difference is sufficient to be discernible by the human over the color space difference of 4.8 afforded by the untreated filter paper matrix of FIG. 1. Similarly, an assayer can visually detect Bence Jones proteins in a test sample because the color space difference between a 100 mg/dL solution of Bence Jones proteins and a 0 mg/dL solution of Bence Jones proteins is 13.0, compared to a color space difference of 4.4 when an indicator reagent composition is incorporated into untreated filter paper, or a 195% improvement. Such a color difference is more than sufficient to allow color differentiation by the human eye. Similarly, TABLE I and FIG. 2 shows enhanced color differentiation for the 20 mg/dL, 30 mg/dL, 100 mg/dL and 500 mg/dL albumin solutions compared to the solution containing no albumin.

Overall, FIGS. 1 and 2 and TABLE I show that an indicator reagent composition impregnated into a carrier matrix comprising a fibrous, bibulous substrate homogeneously impregnated with a polymerized urethane-based compound from the urethane-containing composition of Example 1 improves color resolution and assay sensitivity in the assay for the total protein content of a liquid test sample, especially at low protein levels of less than 30 mg/dL. The method and device allow visual differentiation of color transitions resulting from contact of the indicator reagent-containing carrier matrix with a test sample containing protein at levels of between 0 mg/dL and 10 mg/dL, thereby providing more accurate and trustworthy assays.

The method and device of the present invention, as further shown in FIGS. 1 and 2 and TABLE I, improve the ability of the test strip to detect Bence Jones proteins. Present day test strips, comprising an indicator reagent composition impregnated into a filter paper matrix, detect a concentration of 100 mg/dL Bence Jones proteins as equivalent to a trace amount, or about 10 to about 15 mg/dL, of albumin. For example, from TABLE I and FIG. 1, $\Delta E(Alb\ 10\text{-}0)$ is 4.8, whereas $\Delta E(BJ\ 100\text{-}0)$ is 4.4. However, a test strip of the present invention, having a test pad comprising an indicator reagent composition incorporated into a carrier matrix comprising a fibrous, bibulous matrix homogeneously impregnated with a polymerized urethane-based compound, improves the detection of 100 mg/dL Bence-Jones protein in a test sample by about one color block, or as equivalent to 30 mg/dL of albumin. For example, from TABLE I and FIG. 2, $\Delta E(Alb\ 30\text{-}0)$ is 16.8 and $\Delta E(BJ\ 100\text{-}0)$ is 13.0. Accordingly, Bence Jones proteins in a test sample are detected more easily because of the more spectacular color transition provided by the test strip and method of the present invention.

However, a carrier matrix impregnated with a polymerized urethane-based compound from the urethane-containing composition of Example 1, therein the liquid vehicle includes only dimethylformamide, developed an interfering green background color during manufacture of the carrier matrix. Although the carrier matrix comprising filter paper impregnated with a polymerized urethane-based compound afforded improved assay sensitivity over an untreated filter paper, the "greening" of the carrier matrix interferes in the analysis of protein levels, especially low protein levels, in a liquid test sample by shifting the background color of the carrier matrix by approximately one to approximately two color blocks towards the green region of the color space. Consequently, elimination of the interfering green background color of the carrier matrix would further improve the sensitivity of the dry phase test strip assay for proteins in a liquid test sample.

Surprisingly and unexpectedly, it has been found that a liquid vehicle comprising an aprotic solvent, such as dimethylformamide, and an alcohol essentially eliminates the "greening" problem. Therefore, more accurate protein determinations are achieved. In addition, the essential elimination of the interfering green background color of the carrier matrix further provides a method to quickly and accurately test for Bence Jones proteins and other low molecular weight proteins in a test sample by providing a carrier matrix that sufficiently improves assay sensitivity to allow detection and measurement of low concentrations of low molecular weight proteins. Furthermore, utilizing a liquid vehicle comprising an aprotic solvent and an alcohol allows the urethane-containing composition to be cured in a shorter time.

Consequently, it has been found that impregnating a fibrous bibulous substrate with a urethane-containing composition including a liquid vehicle comprising an aprotic solvent and an alcohol yields, after curing, a non-greening carrier matrix that further improves the accuracy and precision of dry phase test strip protein assays. Aprotic solvents, like dimethylformamide, are generally unpleasant solvents. Therefore reducing the amount of aprotic solvent in the liquid vehicle by including from about 30% to about 70% by weight of an alcohol not only improves assay sensitivity, but facilitates manufacture of dry phase test strips by reducing unpleasant odors and shortening curing times.

In accordance with an important feature of the present invention, it has been demonstrated that by dissolving or dispersing the urethane compound in a liquid vehicle comprising from about 30% to about 70% by weight of an aprotic solvent, like dimethylformamide, and from about 30% to about 70%, and preferably from about 40% about 50%, by weight of an alcohol, such as methyl alcohol, ethyl alcohol or isopropyl alcohol, that the development of an interfering green background color in the carrier matrix is essentially eliminated. The interfering green background color is observed when an aprotic solvent is used exclusively as the liquid vehicle of the urethane-containing composition. Further advantages found by using a liquid vehicle comprising an aprotic solvent and an alcohol include a reduced curing time of the urethane-containing composition to as low as about 30 seconds; a reduction of unpleasant aprotic solvent odors; and a greater response, and therefore an increased sensitivity, to Bence Jones protein in a liquid test sample.

To demonstrate the benefits of using a dry phase test strip including a test pad comprising the non-greening and non-bleeding carrier matrix of the present invention, TABLE II shows color space differences ($\Delta E$) values for protein analyses performed by dipping a dry phase test strip into a standard sample containing a known amount of albumin or Bence Jones protein. The test strips comprise test pads including an indicator reagent composition incorporated into a fibrous, bibulous substrate impregnated with a polymerized urethane-containing compound from either the composition of Example 1, Example 2, Example 3 or Example 4. The color transition of the dry phase test strip was determined, either visually or by instrument, one minute after dipping the test strip into the liquid test sample.

TABLE II

| EXAMPLE | LIQUID VEHICLE | CURING TIME | Alb0* | Alb10 | Alb20 | Alb30 | Alb100 | BJ100 | % BJ/Alb** |
|---|---|---|---|---|---|---|---|---|---|
| 1 | DMF | 30 sec | — | — | — | — | — | — | — |
| 2 | DMF/MeOH | 30 sec | 3.92 | 10.49 | 15.31 | 21.95 | 39.93 | 21.96 | 55 |
| 3 | DMF/EtOH | 30 sec | 13.35 | 19.54 | 24.93 | 27.71 | 42.73 | 35.90 | 84 |
| 4 | DMF/IPA | 30 sec | 14.92 | 19.12 | 25.72 | 29.33 | 42.01 | 37.80 | 90 |

TABLE II-continued

| EXAMPLE | LIQUID VEHICLE | CURING TIME | Alb0* | Alb10 | Alb20 | Alb30 | Alb100 | BJ100 | % BJ/Alb** |
|---|---|---|---|---|---|---|---|---|---|
| 1 | DMF | 1 min | 12.37 | 16.60 | 19.52 | 23.40 | 38.41 | 23.52 | 61 |
| 2 | DMF/MeOH | 1 min | 2.90 | 8.79 | 18.33 | 22.28 | 45.08 | 22.86 | 51 |
| 3 | DMF/EtOH | 1 min | 5.56 | 10.56 | 18.34 | 22.02 | 44.60 | 28.07 | 63 |
| 4 | DMF/IPA | 1 min | 4.86 | 11.41 | 18.53 | 24.59 | 44.96 | 26.69 | 59 |
| 1 | DMF | 2 min | 3.51 | 9.98 | 14.45 | 18.90 | 39.60 | 18.24 | 46 |
| 2 | DMF/MeOH | 2 min | 2.42 | 9.30 | 17.82 | 22.82 | 44.13 | 25.24 | 57 |
| 3 | DMF/EtOH | 2 min | 2.75 | 10.03 | 16.83 | 21.20 | 44.85 | 25.60 | 57 |
| 4 | DMF/IPA | 2 min | 3.75 | 10.29 | 16.50 | 22.33 | 47.97 | 28.31 | 59 |
| 1 | DMF | 5 min | 0 | 6.29 | 13.09 | 15.55 | 37.20 | 11.02 | 30 |

*Protein levels measured in mg/dL. Alb = Albumin, BJ = Bence Jones
**Ratio of ΔE values at Bence Jones (100 mg/dL) to Albumin (100 mg/dL)
DMF - dimethylformamide; MeOH - methanol; EtOH - ethanol; IPA - isopropyl alcohol
DMF - Example 1, DMF/MeOH - Example 2, DMF/EtOH - Example 3; DMF/IPA - Example 4

From TABLE II, it is demonstrated that, when dimethylformamide (DMF) is used as the liquid vehicle (EX. 1), the urethane-containing composition does not cure in 30 seconds. In addition, each test strip impregnated with a urethane-containing composition including only DMF as the carrier vehicle developed a green background color. Accordingly, quantitative color space differences (ΔE) were not determined for standardized solutions including from 0 mg/dL to 100 mg/dL albumin, or for the standardized solution including 100 mg/dL Bence Jones proteins. However, it is envisioned that the color space difference essentially would not change between a solution having 0 mg/dL albumin and a solution having 100 mg/dL albumin. Conversely, it was found that a liquid vehicle comprising DMF and an alcohol (EXS. 2–4) does cure the urethane-containing composition in 30 seconds.

Figure 3:
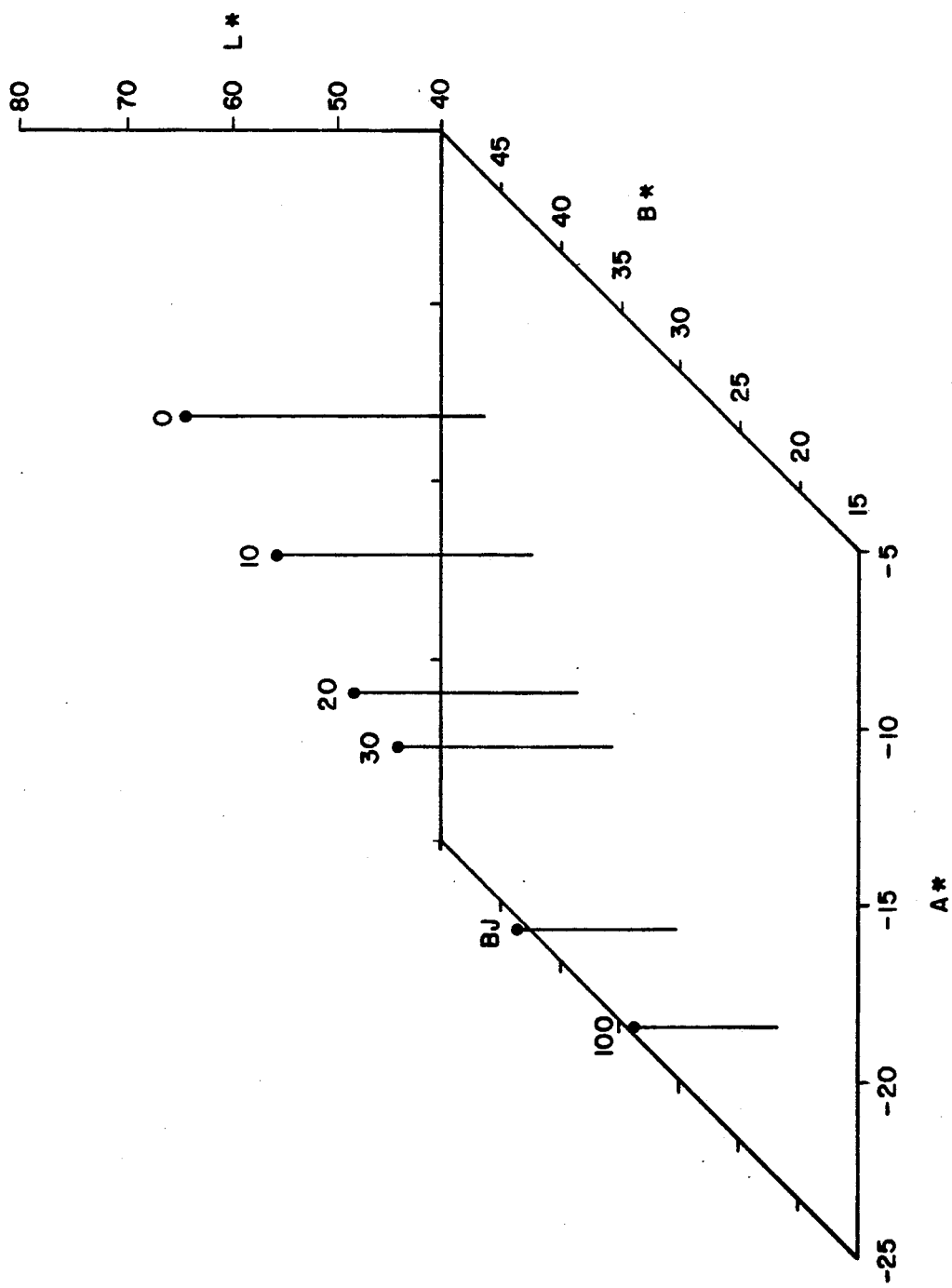
FIG. 3 is a color space plot showing the assay of liquid samples containing 0, 10, 20, 30 and 100 mg/dL of albumin respectively and 100 mg/dL of Bence Jones proteins using a dry phase test strip utilizing a carrier matrix comprising a filter paper substrate homogeneously impregnated with a polymerized urethane-based compound, and incorporating the indicator dye tetrabromophenol blue (TBPB), wherein the impregnated filter paper was cured in a water bath for 30 seconds after impregnation with a urethane-containing composition.
Figure 4:
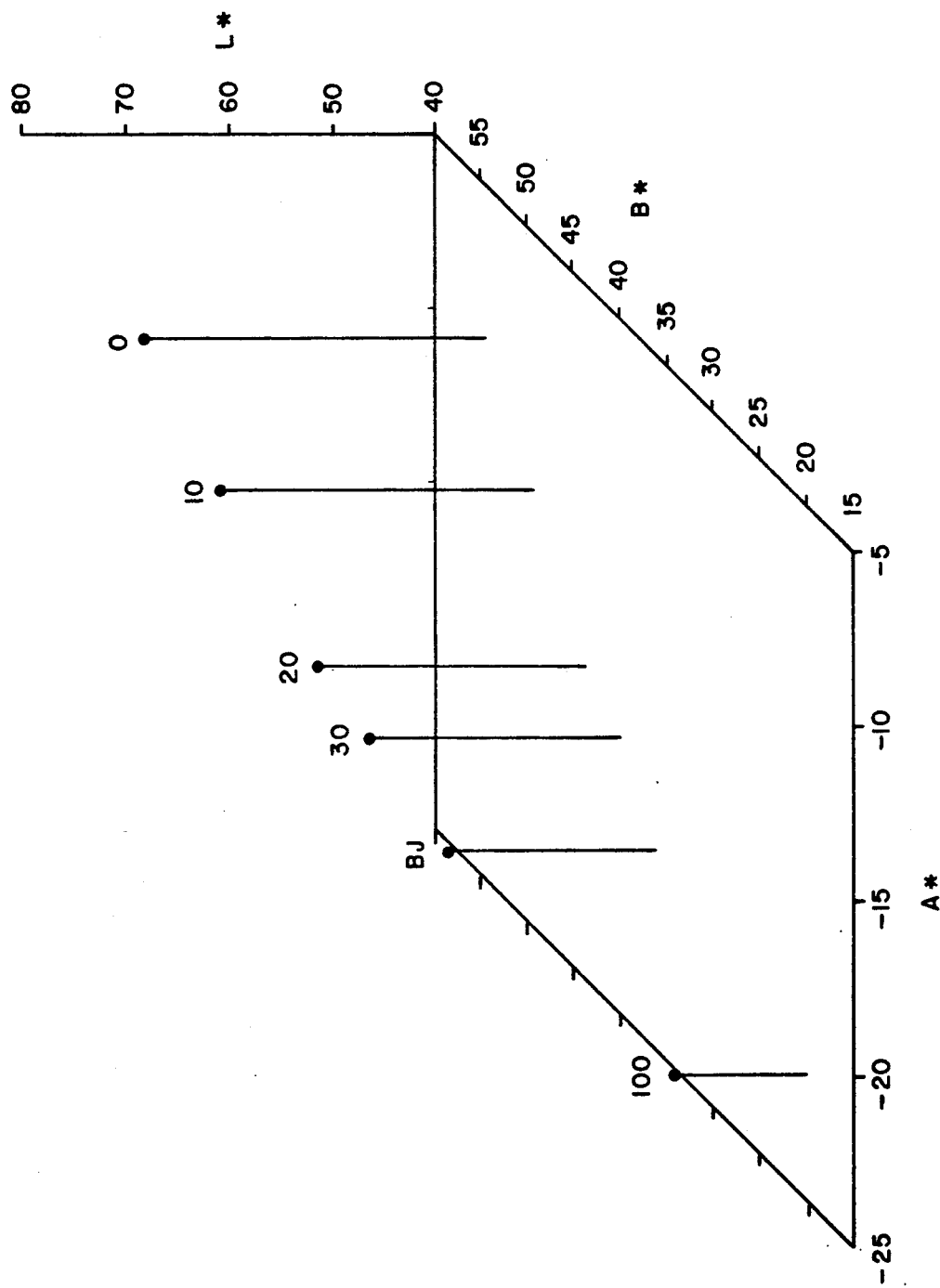
FIG. 4 is a color space plot similar to the color space plot of FIG. 3, except the impregnated filter paper was cured in a water bath for 1 minute after impregnation with a urethane-containing composition.
Figure 5:
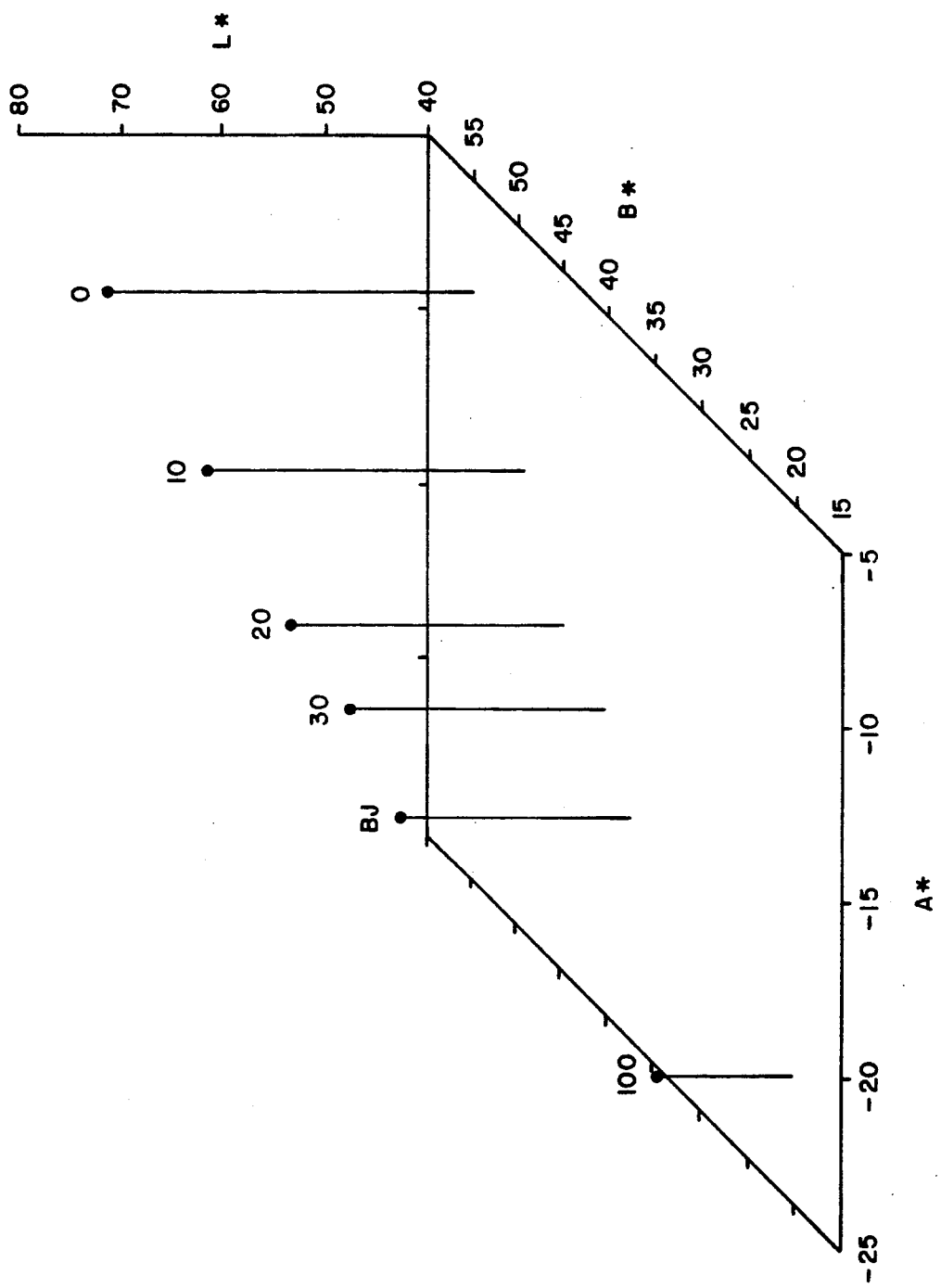
FIG. 5 is a color space plot similar to the color space plots of FIGS. 3 and 4, except the impregnated filter paper was cured in a water bath for 2 minutes after impregnation with a urethane-containing composition.

Further, from TABLE II and FIGS. 3–5, it is shown that the non-greening carrier matrix of the present invention improves the sensitivity of dry phase test strip assays for protein compared to dry phase test strips utilizing an untreated filter paper carrier matrix (FIG. 1) and compared to dry phase test strips utilizing a carrier matrix comprising filter paper impregnated with a polymerized urethane-based compound from the urethane containing composition of Example 1 (FIG. 2). For example, in interpreting the data presented in TABLE II, the color space differences (ΔE) are referenced to the 5 minute water-curing data demonstrated by a urethane-containing composition utilizing DMF as the liquid vehicle (EX. 1). In general, the data in TABLE II illustrate two important improvements. First, the smallest ΔE values for the blanks, i.e., (Alb 0), for each solvent combination and water curing time are examined. A color space difference of zero indicates complete removal of DMF from the carrier matrix. Large color space differences indicate incomplete DMF removal from the carrier matrix. Accordingly, it was demonstrated that the development of green background color is essentially eliminated when the carrier matrix is water-cured for 2 minutes. For a one minute curing time, only the carrier matrix impregnated with the composition of Example 1, i.e., DMF only, demonstrated a substantial greening effect, wherein all the carrier matrices impregnated with a composition including a DMF/alcohol combination, i.e., Examples 2 through 4, demonstrated either no green, or a trace of green, background color. Accordingly, using a DMF/alcohol combination as the liquid vehicle of the composition, as opposed to only DMF, provided a distinct improvement in eliminating the development of a green background color.

To demonstrate a second improvement, the greatest ΔE values for the test samples including protein are examined (i.e., Alb 10 through Alb 100). A large ΔE value indicates better color resolution and a more reliable color differentiation between test samples having different concentrations of protein. Accordingly, carrier matrices impregnated with compositions having a DMF/alcohol combination as the liquid vehicle demonstrate improved sensitivity compared to carrier matrices impregnated with compositions having only DMF as the liquid vehicle. For example, a test solution including 100 mg/dL of albumin (Alb 100), impregnated with a composition including only DMF as the liquid vehicle (EX. 1) and with 2 minute curing time, demonstrates a ΔE of 39.60, whereas carrier matrices impregnated with compositions including a DMF/alcohol combinations as the liquid vehicle (EXS. 2–4) gave a ΔE of from 44.13 to 47.97, or a one color block improvement. These two improvements show that a partial replacement of DMF by an alcohol in the urethane-containing composition provided increased test strip performance in the assay for proteins. In addition, the choice of a particular alcohol to include as a partial replacement for DMF in the urethane-containing composition is not extremely critical. However, to achieve the full advantage of the present invention, ethanol or isopropyl alcohol is used to partially replace the DMF in the urethane-containing composition, primarily because of toxicity considerations.

Therefore, it has been demonstrated that color space differences are improved by using the non-greening carrier matrix of the present invention in a dry phase test strip assay for proteins. Accordingly, the improved carrier matrix of the present invention essentially eliminates the development of a green background color and improves the color response of a dry phase test strip to proteins in a test sample. Therefore, because the background color of the test pad maintained in the yellow region of the color space, an improved color differentiation between the low albumin concentrations, such as less than about 30 mg/dL albumin, is achieved.

In addition, employing the non-greening carrier matrix of the present invention dramatically increased the assay sensitivity to low molecular weight proteins, therefore providing a simple, dry phase test strip procedure to assay for low molecular weight proteins. As demonstrated in FIGS. 1 and 2 and in TABLE I, assaying a solution containing 100 mg/dL of Bence Jones proteins with a test device having an indicator reagent composition incorporated into an untreated filter paper matrix gave an imperceptible color difference of 4.4 compared to assaying a solution containing no Bence Jones proteins. However, color resolution and assay sensitivity is improved by incorporating the same indicator reagent composition into a carrier matrix comprising a fibrous, bibulous substrate impregnated with a polymerized urethane-based compound such that the color difference is a readily perceptible 13.0. Furthermore, TABLE II shows that the color space difference for a test sample including 100 mg/dL Bence Jones proteins generally is greater than the color space difference for a test sample including 30 mg/dL albumin. Accordingly, a test strip of the present invention demonstrates a substantial improvement over present day test strips that provide a color space difference for a test sample including 100 mg/dL Bence Jones proteins approximately equivalent to the color space difference provided by a sample including 15 mg/dL albumin. Therefore, a test device of the present invention provides a more spectacular color development, and Bence Jones proteins therefore are more easily detected.

In addition to eliminating the development of an interfering green background color of the carrier matrix, the carrier matrix of the present invention also demonstrated an ability to substantially reduce or eliminate the tendency of the indicator reagent composition to bleed from the carrier matrix when the test pad is wetted by a liquid test sample. Such a non-bleeding feature is especially advantageous in a multideterminant dry phase test strip that simultaneously assays a single liquid test sample for several test sample constituents.

For example, a multideterminant test strip for urine can include up to about ten individual test pads on a single test strip to assay a urine sample for pH, protein, glucose, bilirubin, nitrite, specific gravity, blood, ketones, urobilinogen and leukocyte esterase. Each test pad includes a specific indicator reagent composition to assay for a particular urinary constituent. Consequently, it is important that the indicator reagent composition incorporated in one test pad does not bleed onto an adjacent test pad to contaminate the adjacent test pad, and thereby interfere with the assay performed by the adjacent test pad to provide an inaccurate and unreliable assay.

More specifically, in many multideterminant test strips for assaying urine, the test pad for a protein assay is positioned adjacent to the test pad for urine pH. As previously discussed, the indicator reagent composition incorporated in the protein test pad is buffered at an acidic pH, such as a pH of about 3 to about 4, like a pH of 3.3 with a citrate buffer. However, the normal pH of urine is in the range from about 4.6 to about 8. Consequently, when a multideterminant test strip is dipped into a urine test sample, a portion of the acid-buffered indicator reagent composition incorporated into the protein pad can be extracted and carried by the urine sample onto the adjacent pH pad. Accordingly, the pH assay is adversely affected and can provide an erroneously low assay. This phenomenon is known in the art as reagent "runover", and has been a continuing and unsolved problem with multideterminant test strips since their inception.

Therefore, an appreciable amount of bleeding, or runover, of the acid-buffered protein indicator reagent composition onto the adjacent urine pH test pad could provide an assay for urine pH that is inaccurate and unreliable, and may result in an incorrect diagnosis. Surprisingly and unexpectedly, the new and improved carrier matrix of the present invention not only resists the development of a green background color, thereby providing a more accurate protein assay; but also essentially eliminates the runover of the protein indicator reagent composition from the carrier matrix, thereby precluding contamination of, and assay interference with, adjacent test pads, for example a pH assay. Therefore, the carrier matrix of the present invention also allows a more accurate and reliable assay to be performed by an adjacent test pad. Consequently, it has been found that the inexpensively-manufactured carrier matrix of the present invention, comprising a fibrous, bibulous substrate impregnated with a polymerized urethane-based compound, essentially eliminates the problem of indicator reagent composition runover onto adjacent test pads. Although the previously-cited prior art shows that polyurethane have been used to treat paper and paper products, none of these prior art references, alone or in combination, teaches or suggests the use of a fibrous, bibulous substrate impregnated with a polymerized urethane-based compound in a clinical diagnostic device to prevent an indicator reagent composition from bleeding from the impregnated substrate.

To demonstrate the new and unexpected results achieved by non-greening and non-bleeding carrier matrix of the present invention, a solution including 2% by weight of a neutral urethane prepolymer, DESMODERM KBH; 50.3% by weight dimethylformamide; and 47.7% by weight ethyl alcohol (EX. 3) was prepared. A sheet of WHATMAN CCP500 filter paper was impregnated with the solution of Example 3, and the urethane-containing composition was cured onto the filter paper by placing the impregnated filter paper into a 24° C. water bath for about 2 minutes. Then the impregnated filter paper was dried in an 80° C. oven for about 20 minutes. The dried, impregnated filter paper then had incorporated therein an aqueous indicator reagent composition including tetrabromophenol blue (TBPB) buffered to a pH of about 3.3 with a citrate buffer. After again drying in an 80° C. oven for about 20 minutes, the carrier matrix incorporating the indicator reagent composition was cut into strips, then pads. Then multideterminant test strips for urine were prepared that included a pH test pad positioned adjacent to a protein test pad manufactured as described above (A Strips). The A Strips were compared to multideterminant test strips having a pH test pad positioned adjacent to a protein test pad comprising a tetrabromophenol blue/citrate indicator reagent composition impregnated into a carrier matrix of untreated WHATMAN CCP500 filter paper (B Strips) and to commercially-available multideterminant test strips.

Repeated experiments demonstrated that upon briefly dipping an A Strip into a urine sample having a relatively high pH of about 8, the color of the pH assay pad underwent a color transition of from orange to green, thereby correctly assaying the urine pH. In contrast, when a present day, commercial protein test pad, ALBUSTIX, available from Miles, Inc., Elkhart, Ind., was positioned adjacent to a pH test in a multideterminant test strip, upon dipping the strip briefly into the same urine sample, the pH test pad on the test strip was either partially or entirely orange in color, thereby indicating a severe runover of the acidic buffer from the ALBUSTIX protein pad onto the pH pad. The ALBUSTIX protein pad comprises a tetrabromophenol blue/citrate indicator reagent composition impregnated into a carrier matrix including filter paper. Consequently, it was shown that the new carrier matrix of the present invention essentially eliminated the problem of indicator reagent composition runover found in present-day protein test pads.

Furthermore, upon briefly dipping a B Strip into a urine sample having a pH of about 8, it was found that reagent runover, i.e., a color transition to orange in the pH test pad, was observed in two of the eight B Strips that were tested. This high runover rate of 25% of the tested strips is unacceptable in regard to obtaining an accurate and reliable pH assay, and further demonstrates that impregnation of the fibrous, bibulous substrate with a polymerized urethane-based compound effectively eliminates indicator reagent composition runover from the carrier matrix.

In accordance with another important feature of the present invention, test strips were manufactured in an identical manner to the manufacture of the A Strips, except that the WHATMAN CCP500 filter paper was impregnated with a solution that included 2% by weight of the anionic urethane prepolymer DESMODERM DLH in place of the neutral urethane prepolymer DESMODERM KBH. Carrier matrices including a cured fibrous, bibulous substrate impregnated with the DESMODERM DLH containing solution, also showed an ability to essentially eliminate indicator reagent composition runover when compared to ALBUSTIX protein test pads and to the B Strip. Consequently, indicator reagent composition runover can be eliminated by impregnating a fibrous, bibulous substrate with a neutral polymerized urethane-based compound, a cationic polymerized urethane-based compound, or a combination thereof.

To further demonstrate the ability of the carrier matrix of the present invention to essentially eliminate indicator reagent composition runover, four commercially-available multideterminant test strips, MULTISTIX 10 SG, Miles Inc., Elkhart, Ind., were dipped into urine having a pH of about 7.5. The MULTISTIX 10 SG test strips include an ALBUSTIX test pad to perform the protein assay. In each of the four tests, the pH assay pad demonstrated a find color of orange, either totally or mixed with some green color, thereby showing several indicator reagent composition runover from the protein assay pad. Then, in four fresh MULTISTIX 10 SG test strips, the ALBUSTIX protein assay pad was removed and replaced by a protein assay pad of the present invention including a carrier matrix comprising a fibrous, bibulous substrate impregnated with a polymerized urethane-based compound. After dipping those four multideterminant test pads into a urine sample having a pH of about 7.5, the pH assay pad underwent a color transition from orange to green, thereby providing an accurate pH assay and demonstrating that the carrier matrix of the present invention effectively eliminates indicator reagent composition runover from the protein assay pad.

Therefore, in accordance with an important feature of the present invention, more accurate and reliable assays for total protein content, or for low molecular weight protein content, in urine and other liquid test samples can be performed by utilizing the non-greening invention in a dry phase test strip assay for proteins. The non-greening carrier matrix of the present invention effectively resists the development of an interfering green background color and therefore improves the color resolution of the assay and improves assay sensitivity, especially at low albumin levels of approximately 30 mg/dL and below. Furthermore, by performing the assay with a dry phase test strip that includes the non-greening carrier matrix of the present invention, a new and unexpectedly accurate method of determining the presence or concentration of low molecular weight proteins, like. Bence Jones proteins, in the test sample is provided In addition, and in accordance with another important feature of the present invention, more accurate and reliable assays for other constituents, such as pH, in urine and other liquid test samples can be performed by utilizing the non-greening and non-bleeding carrier matrix of the present invention in a dry phase test strip assay for proteins. The non-bleeding carrier matrix of the present invention essentially eliminates the bleeding, or runover, of the indicator reagent composition from the carrier matrix, and therefore eliminates interferences with assays performed by adjacent test pads in a multideterminant test strip. Consequently, the carrier matrix of the present invention not only provides more accurate protein assays, but also unexpectedly provides for the more accurate assay of other test sample constituents performed by adjacent, or nearby, test pads.

Obviously, many modifications and variations of the invention as hereinbefore set forth can be made without departing from the spirit and scope thereof and therefore only such limitations should be imposed as are indicated by the appended claims.

What is claimed and sought to be secured by Letters Patent of the United States is:

1. A method of manufacturing a test pad for determining the presence or concentration of a predetermined chemical compound in a test fluid comprising:

contacting a fibrous, bibulous substrate with a sufficient amount of a urethane-containing composition, comprising from about 0.1% to about 10% by weight based on the total weight of the urethane-containing composition of a urethane compound dispersed in a liquid vehicle comprising an aprotic solvent and an alcohol, for retention of a portion of the urethane compound in the substrate;

drying the fibrous, bibulous substrate to remove the liquid vehicle and to form a carrier matrix;

incorporating an indicator reagent composition, capable of a detectable interaction with the predetermined chemical compound, into the carrier matrix to form a test pad that effectively resists the development of a background color and that effectively resists bleeding of the indicator reagent composition from the test pad; and drying the test pad.

2. The method of claim 1 wherein the urethane compound in the urethane-containing composition is a polymerizable urethane compound or a polymerized urethane compound.

3. The method of claim 2 wherein the polymerizable urethane compound in the urethane-containing composition has a weight average molecular weight in the range of from about 30,000 to about 500,000.

4. The method of claim 1 wherein the urethane compound is present in the urethane-containing composition in an amount ranging from about 1% to about 5% by weight based on the total weight of the urethane-containing composition.

5. The method of claim 1 wherein the aprotic solvent is selected from the group consisting of dimethylformamide, dimethylsulfoxide, N-methylpyrrolidone and combinations thereof.

6. The method of claim 1 wherein the aprotic solvent is dimethylformamide.

7. The method of claim 6 wherein the dimethylformamide is present in an amount ranging from about 40% to about 60% by volume of the liquid vehicle and the alcohol is present in an amount ranging from about 40% to about 50% by volume of the liquid vehicle.

8. The method of claim 1 wherein the alcohol is selected from the group consisting of methyl alcohol, ethyl alcohol, isopropyl alcohol and combinations thereof.

9. The method of claim 1 wherein the aprotic solvent is present in an amount ranging from about 30% to about 70% by volume of the liquid vehicle and the alcohol is present in an amount ranging from about 30% to about 70% by volume of the liquid vehicle.

10. The method of claim 1 wherein the liquid vehicle of the urethane-containing composition is present in the urethane-containing composition in an amount ranging from about 85% to about 99.9% by weight based on the total weight of the urethane-containing composition.

11. The method of claim 1 further comprising curing the urethane compound on the fibrous, bibulous substrate prior to drying the fibrous, bibulous substrate.

12. The method of claim 11 wherein the urethane compound on the fibrous, bibulous substrate is cured for a time ranging from about 30 seconds to about 20 minutes by heating the fibrous, bibulous substrate at a temperature in the range of about 30° C. to about 90° C.

13. The method of claim 12 wherein the urethane compound on the fibrous, bibulous substrate is cured for a time ranging from about 30 seconds to about 2 minutes.

14. The method of claim 12 wherein the urethane compound on the fibrous, bibulous substrate is cured in a water bath.

15. The method of claim 11 wherein the fibrous, bibulous substrate is cured for a time ranging from about 30 seconds to about 20 minutes in a sonicator bath containing water.

16. The method of claim 1 wherein the urethane-containing composition further comprises up to about 5% by weight, based on the total weight of the urethane-containing composition, of a surfactant and up to about 2% by weight based on the total weight of the urethane-containing composition, of a silicon-containing material.

17. The method of claim 1 wherein the predetermined chemical compound is a protein.

18. The method of claim 17 wherein the protein is albumin.

19. The method of claim 17 wherein the protein is Bence Jones protein.

20. The method of claim 1 wherein the fibrous, bibulous substrate is selected from the group consisting of filter paper, cloth, hydrophilic natural polymers, hydrophilic synthetic polymers, and hydrophilic modified natural polymers, or mixtures thereof.

21. The method of claim 1 wherein the fibrous, bibulous substrate is filter paper.

22. An analyte detection device to determine the presence or concentration of protein in a liquid test sample comprising a carrier matrix incorporating therein an indicator reagent composition capable of interacting with a protein to produce a detectable and measurable color change in the carrier matrix, wherein the carrier matrix is permeable to the liquid test sample and comprises a fibrous, bibulous substrate homogeneously impregnated with a polymerized urethane-based compound, wherein the polymerized urethane-based compound is impregnated onto the fibrous, bibulous substrate from a urethane-containing composition including from about 0.1% to about 10% by weight of a urethane compound and from about 85% to about 99.9% by weight of a liquid vehicle comprising an aprotic solvent and an alcohol.

23. The analyte detection device of claim 22 wherein the fibrous, bibulous substrate is selected from the group consisting of filter paper, cloth, hydrophilic natural polymers, hydrophilic synthetic polymers, and hydrophilic modified natural polymers, or mixtures thereof.

24. The analyte detection device of claim 22 wherein the fibrous, bibulous substrate is filter paper.

25. A method of determining the presence or concentration of protein in a test fluid comprising:
(a) contacting the test fluid with an analyte detection device comprising a test pad including a carrier matrix and an indicator reagent composition, wherein the indicator reagent composition is capable of exhibiting a detectable response upon interaction with a protein, and wherein the carrier matrix effectively resists development of a green background color and bleeding of the indicator reagent composition from the carrier matrix and comprises a fibrous, bibulous substrate incorporating therein a polymerized urethane compound, wherein the polymerized urethane-based compound is incorporated into the fibrous, bibulous substrate from a urethane-containing composition including from about 0.1% to about 10% by weight of a urethane compound and from about 85% to about 99.9% by weight of a liquid vehicle comprising an aprotic solvent and an alcohol; and
(b) examining the analyte detection device for a response to the protein content of the test fluid.

26. The method of claim 25 wherein the detectable response is a detectable color transition.

27. The method of claim 25 wherein the test fluid comprises a biological test fluid.

28. The method of claim 25 wherein the protein is albumin.

29. The method of claim 28 wherein the test fluid includes 30 mg/dL or less of albumin.

30. The method of claim 28 wherein the test fluid includes 10 mg/dL or less of albumin.

31. The method of claim 25 wherein the protein is Bence Jones proteins.

* * * * *